US012708512B2

(12) United States Patent
Griswold et al.

(10) Patent No.: US 12,708,512 B2
(45) Date of Patent: Aug. 18, 2026

(54) TRANSCATHETER VALVE RECAPTURE DEVICES AND METHODS

(71) Applicant: MEDTRONIC VASCULAR, INC., Santa Rosa, CA (US)

(72) Inventors: Erik Griswold, Penngrove, CA (US); David Grossman, Santa Rosa, CA (US); Radhika Bhargav, Santa Rosa, CA (US); Victoria Tien, Tustin, CA (US); Priya Nair, Shoreview, MN (US)

(73) Assignee: Medtronic Vascular, Inc., Santa Rosa, CA (US)

(*) Notice: Subject to any disclaimer, the term of this patent is extended or adjusted under 35 U.S.C. 154(b) by 1085 days.

(21) Appl. No.: 17/854,634

(22) Filed: Jun. 30, 2022

(65) Prior Publication Data

US 2023/0038490 A1 Feb. 9, 2023

Related U.S. Application Data

(60) Provisional application No. 63/230,300, filed on Aug. 6, 2021.

(51) Int. Cl.

| | |
|---|---|
| ***A61F 2/24*** | (2006.01) |
| ***A61F 2/966*** | (2013.01) |
| *A61F 2/95* | (2013.01) |

(52) U.S. Cl.

CPC ............ *A61F 2/2436* (2013.01); *A61F 2/966* (2013.01); *A61F 2002/9528* (2013.01); *A61F 2002/9534* (2013.01); *A61F 2230/0067* (2013.01)

(58) Field of Classification Search

CPC .................. A61F 2/2436; A61F 2/2418; A61F 2002/9534; A61F 2/2427; A61F 2/243; A61F 2/966; A61F 2002/9528; A61F 2/2439; A61F 2/9522; A61F 2/95; A61F 2210/0014; A61F 2/9525; A61F 2230/0054; A61F 2230/0067

See application file for complete search history.

(56) References Cited

U.S. PATENT DOCUMENTS

| | | | |
|---|---|---|---|
| 8,512,401 | B2 | 8/2013 | Murray, III et al. |
| 9,320,597 | B2 | 4/2016 | Savage et al. |

(Continued)

FOREIGN PATENT DOCUMENTS

| | | | | |
|---|---|---|---|---|
| CN | 1745727 A * | 3/2006 | ........... | A61F 2/2418 |
| EP | 4046604 A1 | 8/2022 | | |

(Continued)

OTHER PUBLICATIONS

Extended European Search Report issued Dec. 21, 2022 in EP Patent Appl. No. 22 18 6246.

(Continued)

*Primary Examiner* — Wesley G Harris
(74) *Attorney, Agent, or Firm* — Medler Ferro Woodhouse & Mills PLLC

(57) ABSTRACT

Delivery catheters for delivery of prosthetic heart valves are provided. The delivery catheters include brim recapture funnels configured for recapture of prosthetic heart valves. The brim recapture funnels are configured to recapture valve brims of partially deployed prosthetic heart valves to reduce or minimize damage to patient anatomy during a valve withdrawal procedure.

17 Claims, 20 Drawing Sheets

(56) References Cited

U.S. PATENT DOCUMENTS

| | | | | |
|---|---|---|---|---|
| 10,271,948 | B2 | 4/2019 | Duffy | |
| 2005/0159770 | A1 | 7/2005 | Divani et al. | |
| 2007/0270932 | A1* | 11/2007 | Headley | A61F 2/95<br>623/1.11 |
| 2010/0049313 | A1* | 2/2010 | Alon | A61F 2/2418<br>623/2.11 |
| 2011/0245917 | A1* | 10/2011 | Savage | A61F 2/2436<br>623/2.11 |
| 2011/0251681 | A1* | 10/2011 | Shipley | A61F 2/243<br>623/2.11 |
| 2011/0251682 | A1 | 10/2011 | Murray, III et al. | |
| 2014/0012369 | A1 | 1/2014 | Murry, III et al. | |
| 2017/0258584 | A1 | 9/2017 | Chang et al. | |
| 2017/0266003 | A1 | 9/2017 | Hammer et al. | |
| 2018/0098848 | A1 | 4/2018 | Tran et al. | |
| 2019/0083246 | A1* | 3/2019 | Hariton | A61F 2/2445 |
| 2020/0281720 | A1 | 9/2020 | Jackson et al. | |
| 2021/0154010 | A1 | 5/2021 | Schneider et al. | |

FOREIGN PATENT DOCUMENTS

| | | | | |
|---|---|---|---|---|
| WO | WO-2009026272 | A1 * | 2/2009 | A61B 17/221 |
| WO | WO-2010096176 | A1 * | 8/2010 | A61F 2/2427 |
| WO | WO-2011043900 | A1 * | 4/2011 | A61F 2/011 |
| WO | WO-2019195336 | A1 * | 10/2019 | A61F 2/2427 |

OTHER PUBLICATIONS

Extended European Search Report, EP Application No. 22186246.9, mail Jan. 4, 2023.

* cited by examiner

FIG. 5
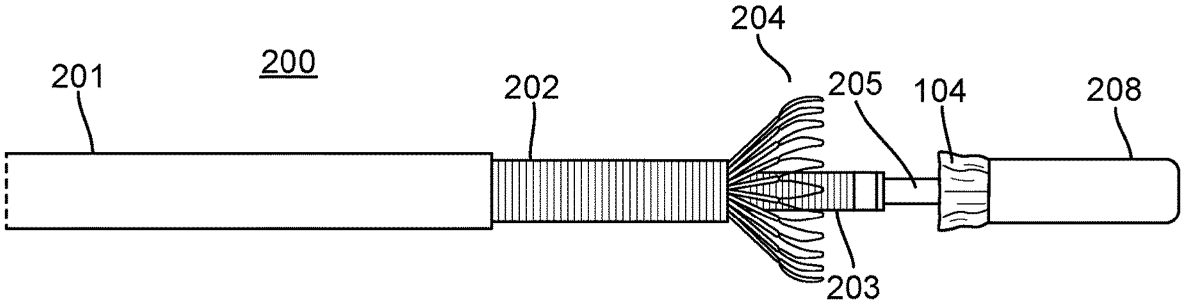
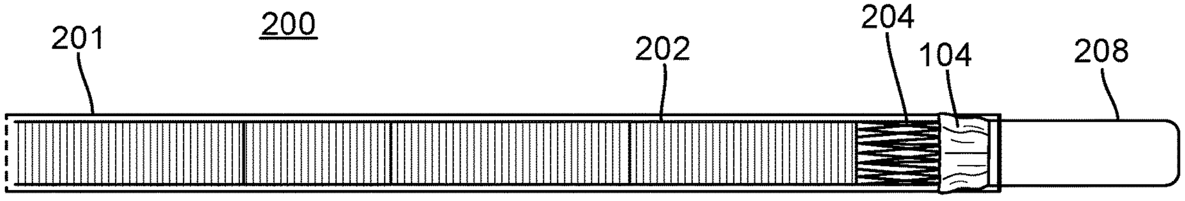
FIG. 6

TRANSCATHETER VALVE RECAPTURE DEVICES AND METHODS

FIELD OF THE INVENTION

The present invention is related to systems and methods for transcatheter valve delivery and deployment. In particular, the present invention is related to transcatheter valve delivery devices configured for recapture of prosthetic heart valves during a valve deployment procedure.

BACKGROUND

Transcatheter valve technology provides a minimally invasive means of implanting prosthetic heart valves. The prosthetic heart valve is loaded onto a delivery system that is able to access and navigate the vasculature to the intended implant location and implant the prosthetic heart valve. A conventional approach for a transcatheter valve system is to use a prosthetic heart valve including a self-expanding stent. After reaching the delivery site, a capsule constraining the prosthetic heart valve is removed and the prosthetic heart valve is released and expands for deployment. After deployment, the capsule is recovered and the catheter is removed from the patient.

During delivery and deployment of a prosthetic heart valve, it may become necessary to recover a partially deployed valve. If there is failure during valve delivery, removal of the prosthetic heart valve may be required. Prosthetic heart valve delivery failure may occur, for example, if the prosthetic heart valve is damaged during deployment. Removal of the partially deployed prosthetic heart valve may be facilitated by retracting the prosthetic heart valve back into the capsule in which it was delivered. In some cases, it may not be possible to return the entirety of the prosthetic heart valve into the capsule. Any portions protruding from the capsule may create a difficulties in removal of the prosthetic heart valve.

Devices and methods disclosed herein address the issue of prosthetic heart valve removal.

SUMMARY

Embodiments hereof relate generally to delivery devices for prosthetic heart valves, and, more specifically, to catheter devices for prosthetic heart valve delivery and deployment. Catheter devices consistent with embodiments hereof may include funnel devices configured to recapture partially deployed prosthetic heart valves.

In an embodiment, a delivery catheter for deploying a self-expanding prosthetic heart valve is provided. The catheter includes an outer steerable catheter, an inner steerable catheter disposed within the outer steerable catheter, an inner compression shaft disposed within the inner steerable catheter, a distal sheath capsule configured to contain a prosthetic heart valve and connected to the inner compression shaft; and a brim recapture funnel configured to recapture a valve brim of a prosthetic heart valve.

In another embodiment, a method of recapturing a prosthetic heart valve with a delivery catheter is provided. The method includes retracting the prosthetic heart valve into a distal sheath capsule of the delivery catheter such that a valve brim of the prosthetic heart valve protrudes from the distal sheath capsule; withdrawing the valve brim into a recapture field of a brim recapture funnel of the delivery catheter; collapsing the brim recapture funnel over the valve brim to capture the valve brim; and withdrawing the delivery catheter and the prosthetic heart valve from patient anatomy.

In still another embodiment, a method of recapturing a prosthetic heart valve with a delivery catheter is provided. The method includes retracting the prosthetic heart valve into a distal sheath capsule of the delivery catheter such that a valve brim of the prosthetic heart valve protrudes from the distal sheath capsule; withdrawing the valve brim into contact with the brim recapture funnel of the delivery catheter; inverting the valve brim over the distal sheath capsule through force provided by the brim recapture funnel; capturing the valve brim by advancing the brim recapture funnel relative to the valve brim; collapsing the brim recapture funnel over the valve brim to capture the valve brim; and withdrawing the delivery catheter and the prosthetic heart valve from patient anatomy.

BRIEF DESCRIPTION OF THE DRAWINGS

The accompanying figures, which are incorporated herein, form part of the specification and illustrate embodiments of a prosthesis delivery system. Together with the description, the figures further explain the principles of and enable a person skilled in the relevant art(s) to make and use the delivery catheters described herein. The drawings are provided to illustrate various features of the embodiments described herein and are not necessarily drawn to scale. In the drawings, like reference numbers indicate identical or functionally similar elements.

FIG. 5 illustrates a recapture delivery catheter including a brim recapture funnel according to embodiments hereof.

FIG. 6 illustrates a recapture delivery catheter including a brim recapture funnel configured for deployment according to embodiments hereof.

DETAILED DESCRIPTION OF THE INVENTION

Specific embodiments of the present invention are now described with reference to the figures. Unless otherwise indicated, for the delivery catheters discussed herein, the terms "distal" and "proximal" are used in the following description with respect to a position or direction relative to the treating clinician or operator. "Distal" and "distally" are positions distant from or in a direction away from the clinician, and "proximal" and "proximally" are positions near or in a direction toward the clinician. As used herein, the term "proximal force" refers to a force in the proximal direction and the term "distal force" refers to a force in the distal direction.

The following detailed description is merely illustrative in nature and is not intended to limit the invention or the application and uses of the invention. Although the description of the invention is in the context of catheter enabled delivery and deployment of prosthetic heart valves, aspects of the invention may also be used in any other context that is useful. As an example, the description of the invention is in the context of delivery and deployment of heart valve prostheses. As used herein, "prosthesis" or "prostheses" may include any prosthesis including an expandable structure. Modifications can be made to the embodiments described herein without departing from the spirit and scope of the present invention. Therefore, the following detailed description is not meant to be limiting. Furthermore, there is no intention to be bound by any expressed or implied theory presented in the preceding technical field, background summary or the following detailed description.

Figure 1:
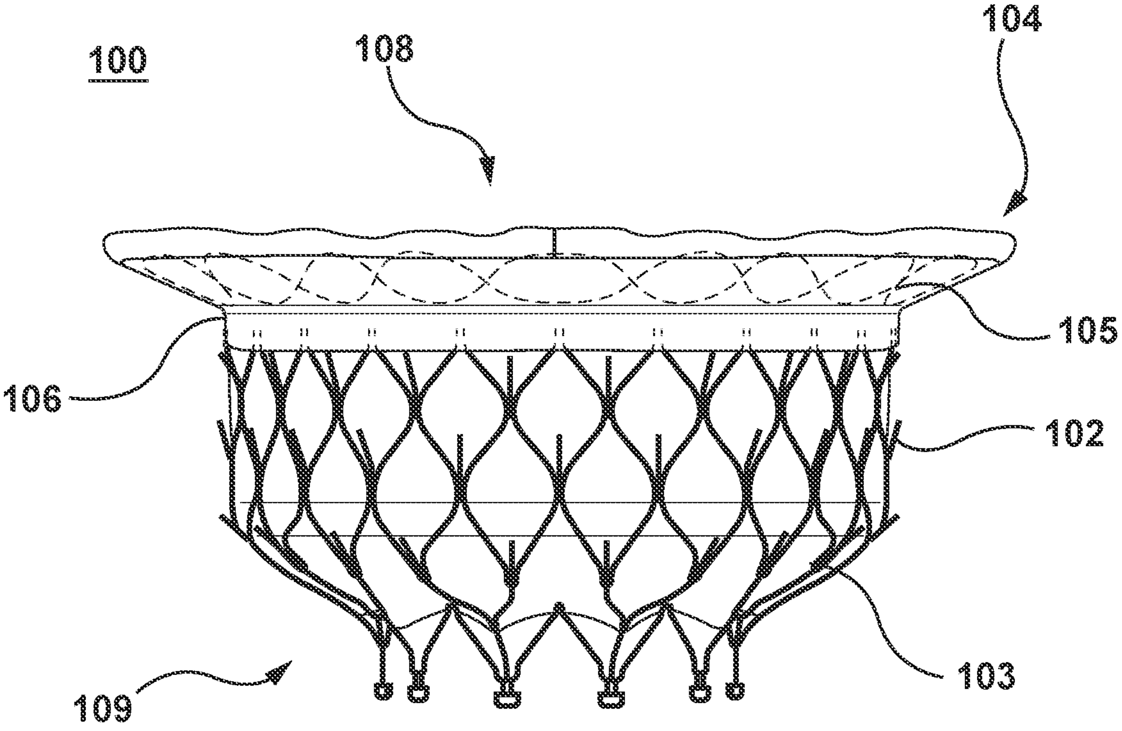
FIG. 1 illustrates a prosthetic heart valve according to embodiments hereof.

FIG. 1 illustrates a prosthetic heart valve 100 consistent with embodiments hereof. The prosthetic heart valve 100 is presented by way of example only, and other shapes and designs of prosthetic heart valves are also consistent with embodiments hereof. Although the prosthetic heart valve 100 is a heart valve prosthesis configured for placement within a mitral heart valve, embodiments of recapture tools and techniques described herein may be used in conjunction with any self-expanding transcatheter valve prostheses. For example, embodiments of recapture tools and techniques described herein may be utilized with a transcatheter prosthetic heart valve configured for placement within a pulmonary, aortic, mitral, or tricuspid valve, or may be utilized with a transcatheter valve prosthesis configured for placement within a venous valve or within other body passageways where it is deemed useful. There is no intention to be bound by any expressed or implied theory presented in the preceding technical field, background, brief summary or the following detailed description.

The prosthetic heart valve 100 is configured to be radially compressed into a reduced-diameter crimped configuration for delivery within a vasculature (not shown) and to return to an expanded, deployed configuration, as shown in FIG. 1. The prosthetic heart valve 100 has a crimped configuration for delivery within a vasculature and an expanded configuration for deployment within a native heart valve or existing prosthetic implant contained within native heart valve anatomy. In accordance with embodiments hereof, when in the crimped configuration, the prosthetic heart valve 100 has a low profile suitable for delivery to and deployment within a native heart valve via a suitable delivery catheter that may be tracked to the deployment site of the native heart valve of a heart via any one of a transseptal, retrograde, or transapical approach. The prosthetic heart valve 100 includes a frame or stent 102 and a prosthetic heart valve component (not shown) secured to the stent 102.

Any portion of the stent 102 described herein as an element of the prosthetic heart valve 100 may be made from any number of suitable biocompatible materials, e.g., stainless steel, nickel titanium alloys such as Nitinol™, cobalt chromium alloys such as MP35N, other alloys such as ELGILOY® (Elgin, Ill.), various polymers, pyrolytic carbon, silicone, polytetrafluoroethylene (PTFE), or any number of other materials or combination of materials. A suitable biocompatible material would be selected to provide the prosthetic heart valve to be configured to be compressed into a reduced-diameter crimped configuration for transcatheter delivery to a native valve, whereby release from a delivery catheter returns the prosthesis to an expanded, deployed configuration, for example, via shape memory or elastic effects.

The prosthetic heart valve 100 includes a proximal end 108 and a distal end 109. The proximal end 108 is an inflow or upstream end and the distal end 109 is an outflow or downstream end. The prosthetic heart valve further include graft material 103 secured to the stent 102 and extending from the proximal end 108 to the distal end 109. At the proximal end 108, the graft material 103 extends past the stent 102. In conjunction with the valve brim support 105, the graft material forms the valve brim 104. The graft material 103 may include any suitable biocompatible low-profile fabric used in bioprosthetic implants namely endovascular grafts, heart valves or left atrial appendage devices to promote bio-integration, such as woven polyethylene terephthalate (PET) fabric. Inside the graft material 103 of the valve brim 104 is a brim support 105, which includes overlapping, 180 degree out of phase sinusoidal wire forms. In further embodiments, the brim support 105 may include alternative supportive elements disposed in alternative configurations. The valve brim 104 may act as an atrial retainer, if present, and to serve such a function the valve brim 104 may be configured to engage tissue above a native annulus, such as a supra-annular surface or some other tissue in the left atrium, to thereby inhibit downstream migration of a prosthetic heart valve 100, for e.g., during atrial systole. Accordingly, the valve brim 104 is of a larger diameter than the stent 102 and extends radially outward from the stent 102 at the proximal end 108 of the prosthetic heart valve 100. The portion of graft material 103 connecting the valve brim 104 to the stent 102 is referred to herein as a valve brim hinge 106. The valve brim hinge 106 is configured to permit the valve brim 104 to hinge and/or flex with respect to the remainder of the prosthetic heart valve 100.

FIGS. 2A-2F illustrate deployment of a prosthetic heart valve according to embodiments hereof. As shown in FIGS. 2A-2F, the prosthetic heart valve 100 is deployed by a delivery catheter 150. The delivery catheter 150 is used to deliver and deploy the prosthetic heart valve 100 to the appropriate cardiac location, e.g., the mitral valve. The delivery catheter 150 includes a distal sheath capsule 151, an inner compression shaft 152, an inner steerable catheter 153, and an outer steerable catheter 154. The inner compression shaft 152 is connected to the distal sheath capsule 151, which houses at least a portion of the prosthetic heart valve 100 during delivery.

The inner compression shaft 152 and distal sheath capsule 151 together may house a hydraulic deployment system (not shown) that is configured to cause proximal and distal translation of the distal sheath capsule 151 with respect to the prosthetic heart valve 100 for deployment. Thus, activation of the hydraulic system may push the distal sheath capsule 151 distally to expose and deploy the prosthetic heart valve 100 and may pull the distal sheath capsule 151 proximally to cover and retract the prosthetic heart valve 100. Hydraulic valve delivery systems consistent with embodiments hereof include, for example, those described in U.S. Pat. No. 9,034,032 to McLean et al., International Patent Application No. PCT/US2014/029549 to McLean et al., and U.S. Pat. No. 10,561,497 to Duffy et al., which are hereby incorporated by reference in their entirety.

Figure 2A:
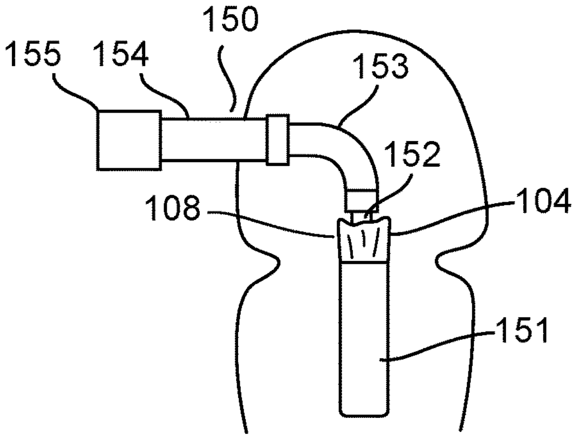
FIGS. 2A-2F illustrate stages in a prosthetic heart valve deployment according to embodiments hereof.
Figure 2B:
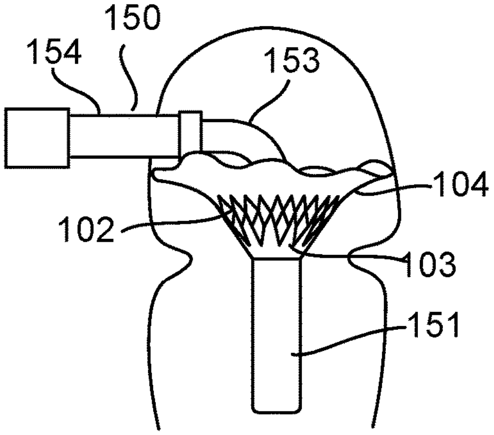
Figure 2C:
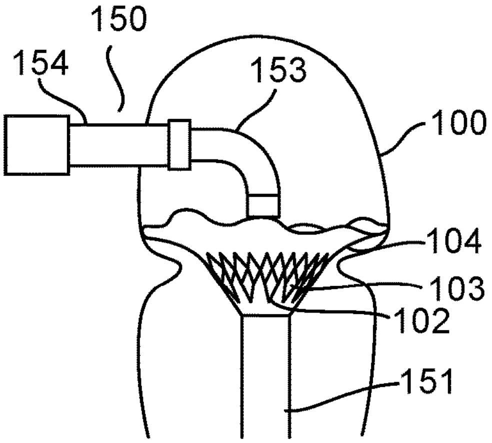
Figure 2D:
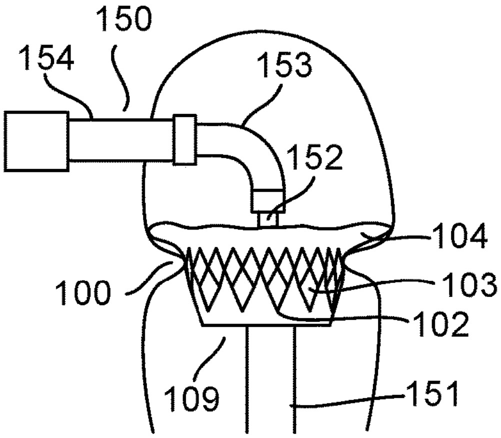
Figure 2E:
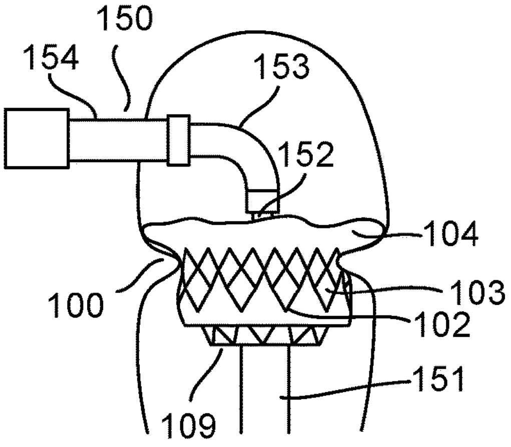
Figure 2F:
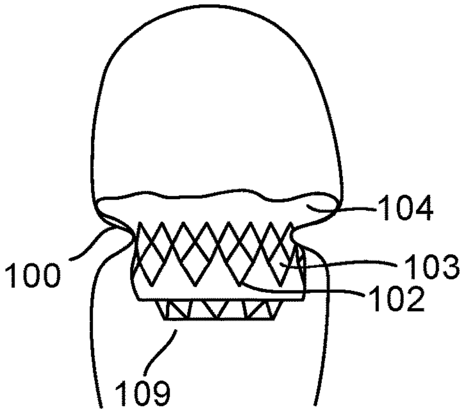

The delivery catheter 150 is delivered to the cardiac location via an introducer sheath 155. During valve deployment, the prosthetic heart valve 100, contained within the distal sheath capsule 151, is steered by the inner steerable catheter 153 and the outer steerable catheter 154 into alignment within the mitral valve for which the prosthetic heart valve 100 serves as a replacement, as shown in FIG. 2A. The hydraulic system within the inner compression shaft 152 is activated to push the distal sheath capsule 151 away from the prosthetic heart valve 100, thereby freeing it. As illustrated in FIG. 2A, at least a portion of the valve brim 104 at the proximal end 108 of the prosthetic heart valve 100 my protrude from the sheath capsule 151 prior to valve release. Release of the prosthetic heart valve 100 proceeds as portions distal of the proximal end 108 are released from the sheath capsule. As the prosthetic heart valve 100 exits the distal sheath capsule 151, the expandable stent 102 expands, as shown in FIG. 2B. This process continues, with the distal sheath capsule 151 being advanced distally of the prosthetic heart valve 100 until the prosthetic heart valve 100 is freed of the distal sheath capsule 151 and is able to fully expand, as shown in FIG. 2D. After releasing the prosthetic heart valve 100, the distal sheath capsule 151 is retrieved through the expanded center of the prosthetic heart valve 100 and the prosthetic heart valve 100 remains within the mitral valve.

During valve deployment, it may become necessary to recover, recapture, or retrieve a partially deployed prosthetic heart valve 100. Such bailout procedures may become necessary when the prosthetic heart valve 100 is mislocated or damaged during deployment. Recovering a partially deployed prosthetic heart valve 100 may present challenges due to the configuration of the valve brim 104. As discussed above, at least a portion of the valve brim 104 may protrude from the sheath capsule 151. During valve delivery, these protruding portions are maintained in a compressed configuration, e.g., via the introducer sheath 155. Further, if the sheath capsule 151 crosses the septum outside of an introducer sheath, the septum itself may maintain compression of the protruding valve brim portion. Returning across the septum, however, may present a challenge. During a return across the septum, if the protruding ends of the valve brim 104 catch or contact tissue, the direction of movement will serve to push the valve brim 104 open further, exacerbating the challenge.

Figure 3A:
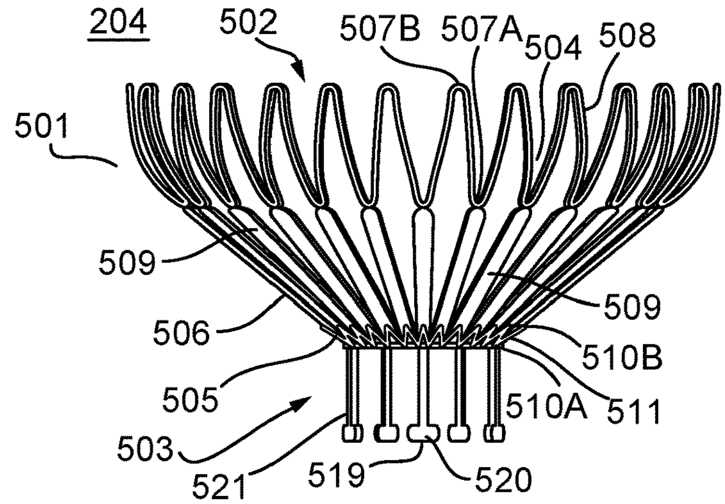
FIG. 3A-3C illustrates the features of a brim recapture funnel.

FIG. 3A illustrates a close-up view of a brim recapture funnel 204 according to embodiments hereof. The brim recapture funnel 204 includes a frame 501. The frame 501 has a distal end 502 and a proximal end 503 and is divided into three portions. The frame 501 includes distal contraction section 504 located at the distal end 502, a proximal contraction section 505 located at the proximal end 503, and a midsection 506 located therebetween. The distal contraction section 504 is configured with a contractable shape, including proximal joints 507A and distal joints 507B and members 508. Each joint 507A, 507B is integrally joined to two members 508. Together, the proximal and distal joints 507A, 507B and the members 508 form a zig-zag or sinusoid pattern. The proximal and distal joints 507A, 507B are flexible facilitate the contraction of the distal contraction section 504 by flexing or bending to change the angle between the members 508 to which they are connected. In embodiments, the distal contraction section 504 is configured with an inward bend or concave shape. The inward bend is formed to direct the tips (i.e., the distal joints 507B) radially inward towards a central axis of the brim recapture funnel 204.

The proximal joints 507A are integrally connected to the midsection 506. The midsection 506 includes a plurality of bars 509. Each bar 509 is connected at a distal end to a proximal joint 507A and at a proximal end to the proximal contraction section 505. The proximal contraction section 505, like the distal contraction section 504, includes a series of proximal joints 510A and distal joints 510B connected by members 511. The proximal contraction section 505 contracts in a similar fashion to that of the distal contraction section 504, by elastic changes in the angles of the proximal and distal joints 510A, 510B.

The brim recapture funnel 204 may be constructed of shape set nitinol. The nitinol structure of the brim recapture funnel 204 is shape set, i.e., through heat treatment, in the "open" configuration illustrated in FIGS. 3A-3C. In further embodiments, the brim recapture funnel 204 may be constructed of alternate materials, such as elgiloy and/or spring steel. In embodiments that do not involve a shape set material, changing between the open configuration and the closed configuration, as discussed below, may be accomplished through elasticity of the structure.

Open configuration refers to a configuration in which the distal joints 507B at the distal end 502 of the brim recapture funnel 204 describe a circle having a diameter larger than that of the proximal end 503. A closed configuration refers to a configuration in which the distal joints 507B at the distal end 502 of the brim recapture funnel 204 describe a circle having a diameter similar to or smaller than that of the proximal end 503. The open configuration of the brim recapture funnel 204 is the configuration of the brim recapture funnel 204 at rest. Through force or pressure directed radially inward, the brim recapture funnel 204 can be forced into the closed configuration according to contraction or compression of the proximal contraction section 505 and the distal contraction section 504. When the force or pressure is released, the brim recapture funnel 204 returns to its resting open configuration. Applying the radially inward force may be achieved through the application of a distally directed force along an axis of the brim recapture funnel 204 applied to the plurality of bars 509. Application of the distally directed force to the bars 509, which are angled with respect to the axis of the brim recapture funnel 204, causes the brim recapture funnel 204 to collapse inwards. Force may also be applied in a distal direction to the proximal contraction section 505 and/or the distal contraction section 504 to collapse the brim recapture funnel 204 inwards. In embodiments, the distally directed force is applied around an entire radius of the funnel 204, for example, by the introducer sheath 201, as described below.

The brim recapture funnel 204 further includes one or more mounting paddles 519. The one or more mounting paddles 519 are integrally connected to the frame 501, for example at the proximal contraction section 505 or the midsection 506. The mounting paddles 519 are T-shaped members that extend proximally from the frame 501. The mounting paddles 519 include a paddle portion 520 and an extension portion 521. A distal end of the extension portion 521 is connected to the frame 501 and a proximal end of the extension portion 521 is connected to the paddle portion 520. The paddle portion 520 is wider than the extension portion 521 and may be rectangular, square, circular, oval, and/or any other suitable shape.

Figure 3B:
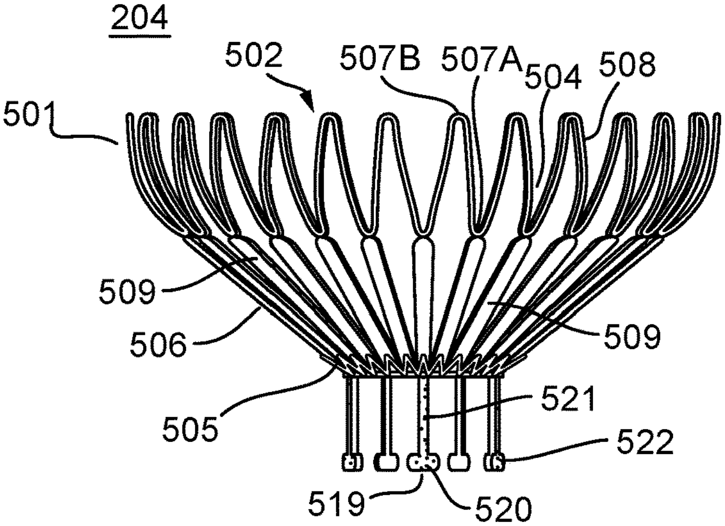

In embodiments, the brim recapture funnel 204 may be constructed with various additional features. For example, all or part of the frame 501 of the brim recapture funnel 204 may be provided with a coating, such as a polymer coating. A polymer coating may include EPTFE or other thin polymer coatings. Polymer coatings may be applied via spraying, dipping, or other suitable technique. A brim recapture funnel 204 including a polymer coating 522 is illustrated in FIG. 3B. The polymer coating 522 may be configured to cover all or a portion of the brim recapture funnel 204. For example, as shown in FIG. 3B, the polymer coating 522 may cover the paddle portion 520. In further examples, the polymer coating may cover the distal joints 507B and a portion of the members 508. In further embodiments, the polymer coating may cover any amount of the brim recapture funnel 204.

Figure 3C:
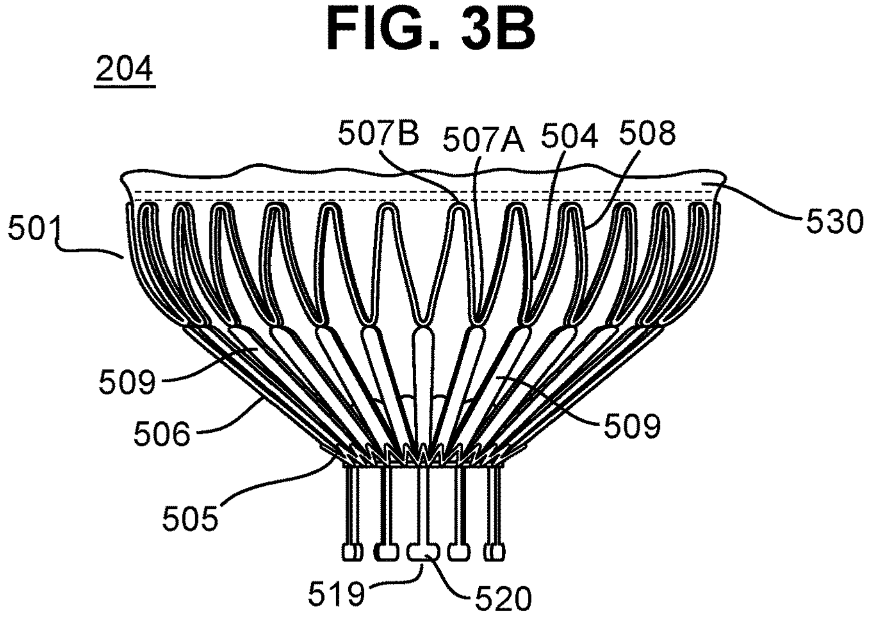

In embodiments, for example as shown in FIG. 3C, the brim recapture funnel may include a flexible covering. A flexible covering 530, including, for example, cloth, plastic, polymer, etc., may be attached to the brim recapture funnel 204. The flexible covering 530 may server to prevent portions of the valve brim from getting caught or stuck in the frame 501 of the brim recapture funnel 204 when the brim recapture funnel 204 is contracted around the valve brim.

Figure 4:
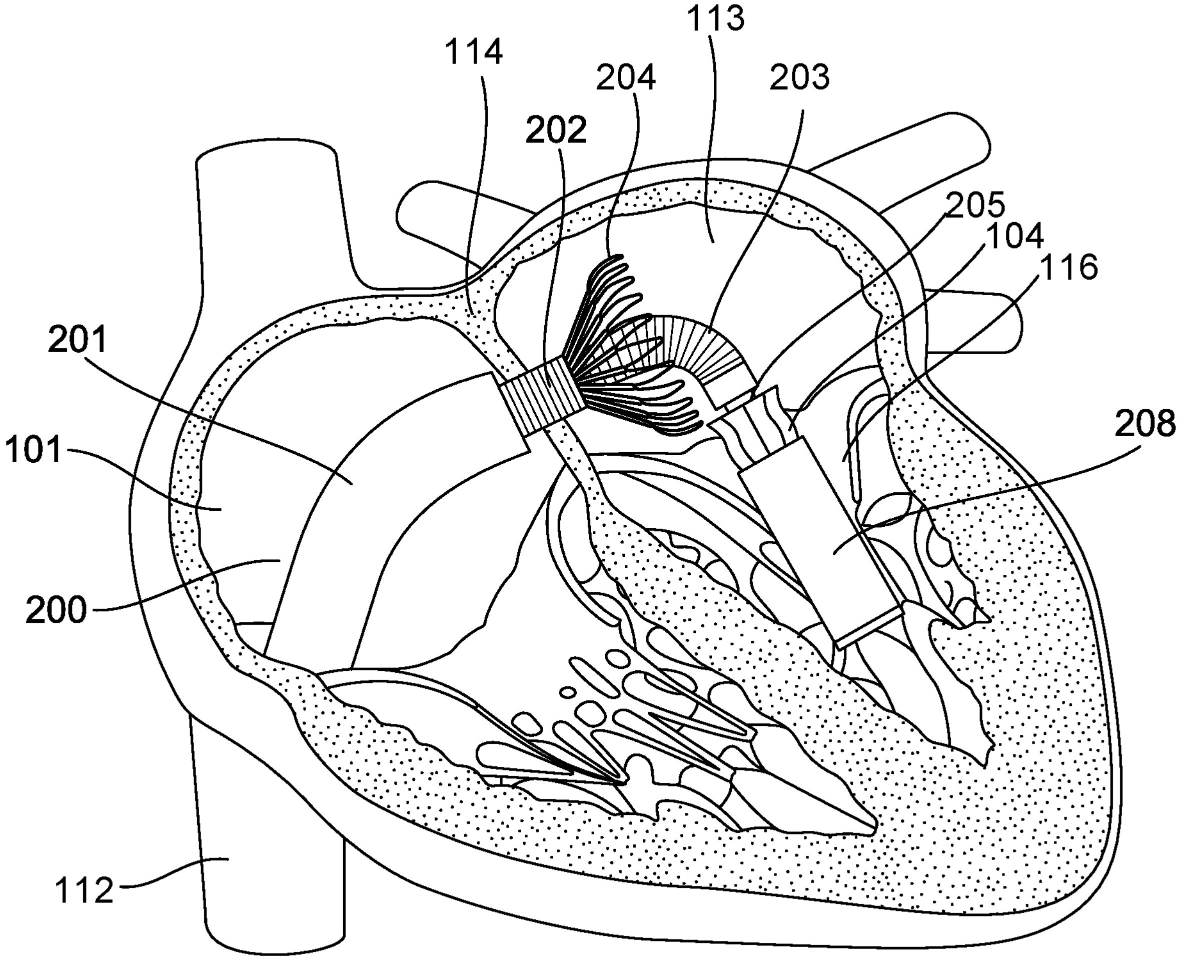
FIG. 4 is an in situ illustration of a delivery catheter including a brim recapture funnel according to embodiments hereof.

FIG. 4 is an in situ illustration of a recapture delivery catheter 200 including the brim recapture funnel 204 being used to deliver a prosthetic heart valve to a mitral valve site according to embodiments hereof. The recapture delivery catheter 200 includes an outer steerable catheter 202, an inner steerable catheter 203, the brim recapture funnel 204, an inner compression shaft 205, and a distal sheath capsule 208. The brim recapture funnel 204 is coupled to the outer steerable catheter 202. Disposed within the distal sheath capsule 208 during delivery is the prosthetic heart valve 100 having the valve brim 104. As shown in FIG. 4, the recapture delivery catheter 200 may be delivered to the deployment site via an introducer sheath 201. The introducer sheath 201 is tracked to the right atrium 101 via the inferior vena cava 112. The introducer sheath 201 may be used to make a transeptal entry into the left atrium 113 across the septum 114. The introducer sheath 201 may be subsequently withdrawn, as shown in FIG. 4. The prosthetic heart valve 100 may be delivered to a mitral valve site 116. Although illustrated with respect to a mitral valve replacement delivery, embodiments of recapture delivery catheters as disclosed herein may be used for any type of valve deployment and recapture.

FIG. 5 illustrates details of the recapture delivery catheter 200 including the brim recapture funnel 204 according to embodiments hereof. As discussed above, the recapture delivery catheter 200 includes an outer steerable catheter 202, an inner steerable catheter 203, a brim recapture funnel 204, an inner compression shaft 205, and a distal sheath capsule 208. The brim recapture funnel 204 is coupled to the outer steerable catheter 202. The recapture delivery catheter 200 may be delivered to a deployment site via an introducer sheath 201. The outer steerable catheter 202 is a flexible, steerable, catheter shaft and may be made of any suitable materials, including stainless steel, polymers, etc. The outer steerable catheter 202 is connected to a recapture delivery catheter handle (not shown) and may be steered and/or actuated via controls built into the handle. The inner steerable catheter 203 is a flexible, steerable, catheter shaft and may be made of any suitable materials, including stainless steel, polymers, etc. The inner steerable catheter 203 is connected to a recapture delivery catheter handle (not shown) and may be steered and/or actuated via controls built into the handle. The inner compression shaft 205 is connected to the distal sheath capsule 208. The distal sheath capsule 208 houses the prosthetic heart valve 100. The inner compression shaft 205 and the distal sheath capsule 208 together house a hydraulic deployment system (not shown) that is configured to cause proximal and distal translation of the distal sheath capsule 208 with respect to the prosthetic heart valve 100 for deployment. Thus, activation of the hydraulic system may push the distal sheath capsule 208 distally to expose and deploy the prosthetic heart valve 100 and may pull the distal sheath capsule 208 proximally to cover and retract the prosthetic heart valve 100.

The configuration shown in FIG. 5 is an operational configuration. During valve delivery and deployment, the inner steerable catheter 203 and the outer steerable catheter 202 are manipulated and steered, via the handle controls, to align the distal sheath capsule 208 housing the prosthetic heart valve 100 with a proper deployment position. The inner compression shaft 205 is used to extend the distal sheath capsule 208 away from the inner steerable catheter 203 and into a proper deployment position. In this configuration, the brim recapture funnel 204 is in an open or extended configuration and is ready to perform a brim recapture should it become necessary.

FIG. 6 illustrates a recapture delivery catheter including a brim recapture funnel in a delivery configuration according to embodiments hereof. In the delivery configuration, the recapture delivery catheter 200 is configured for safe delivery through the introducer sheath, across the septum, and into the left atrium. In the delivery configuration, the brim recapture funnel 204 is folded or collapsed and tucked underneath the valve brim 104. The valve brim 104 and brim recapture funnel 204 are maintained in a closed configuration by virtue of their positioning within the introducer sheath 201. As discussed in greater detail below, the brim recapture funnel 204 is a collapsible funnel and is configured to rest in an open configuration, as illustrated in FIG. 5. When collapsed and tucked underneath the valve brim 104, the brim recapture funnel 204 is maintained in a closed state by force from the valve brim 104, which receives force from the introducer sheath 201.

The deployment configuration of the recapture delivery catheter 200 is configured to facilitate the advancement of the distal sheath capsule 208. As the recapture delivery catheter 200 is advanced distally through an introducer sheath the forces on the distal sheath capsule 208 and the valve brim 104 are directed proximally. Forces in the proximal direction tend to encourage the prosthetic heart valve 100 to remain unexpanded. During deployment, when the introducer sheath 201 is retracted, the valve brim 104 and the brim recapture funnel 204 is freed to expand into the open resting position, as illustrated in FIG. 5.

FIGS. 7A-7F illustrate stages in a valve recapture operation using a recapture delivery catheter according to embodiments hereof. When the introducer sheath 201 is retracted away from the brim recapture funnel 204, the brim recapture funnel 204 expands into the open resting position shown in FIG. 7A.

Figure 7A:
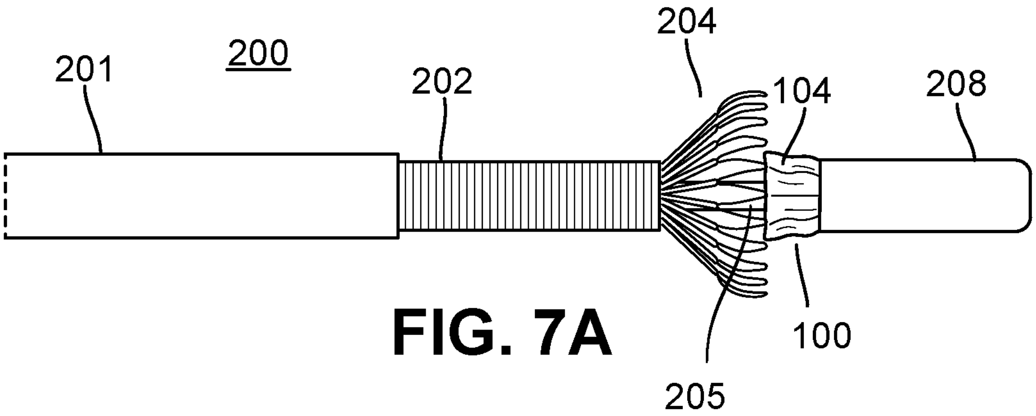
FIGS. 7A-7F illustrate stages in a valve recapture operation using a recapture delivery catheter according to embodiments hereof.
Figure 7B:
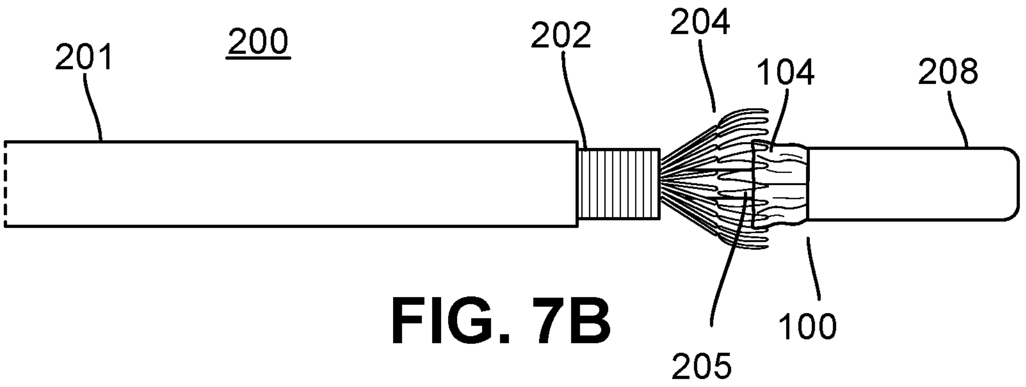

After a failed valve deployment, the hydraulic system of the inner compression shaft 205 (not shown in FIGS. 7A-7F) is used to draw the prosthetic heart valve 100 back into the distal sheath capsule 208 as far as possible. The valve brim 104 continues to protrude proximally from the distal sheath capsule 208. To ensure that the valve brim 104 can be drawn back across the septum without damage to the patient anatomy, the brim recapture funnel 204 is used to capture the valve brim 104. FIG. 7B illustrates the valve brim 104 being brought inside the recapture field of the brim recapture funnel 204. Recapture field refers to the area within which the valve brim 104 must be brought before closing the brim recapture funnel 204 about the valve brim 104. If the valve brim 104 is not within the recapture field when the brim recapture funnel 204 is collapsed for retrieval, the brim recapture funnel 204 will not capture the valve brim 104. The valve brim 104 may be brought into the recapture field through advancement of the outer steerable catheter 202 or retraction of the inner compression shaft 205.

Figure 7C:
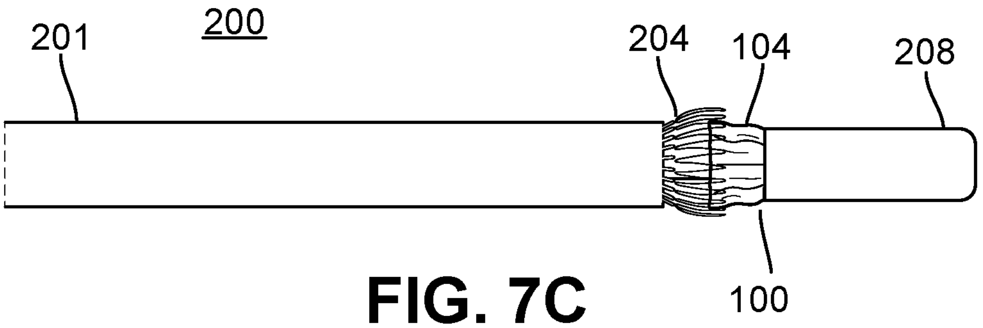

FIG. 7C illustrates the brim recapture funnel 204 beginning to collapse around the valve brim 104 to capture the valve brim 104. After the valve brim 104 has been brought inside the recapture field of the brim recapture funnel 204, the outer steerable catheter 202, the inner steerable catheter 203, and the inner compression shaft 205 are drawn back together into the introducer sheath 201. This may be accomplished by relative movement between the outer steerable catheter 202, the inner steerable catheter 203, and the inner compression shaft 205 against the introducer sheath 201. For example, the outer steerable catheter 202, the inner steerable catheter 203, and the inner compression shaft 205 may be advanced while the introducer sheath 201 is maintained in a stationary position. Alternatively, the introducer sheath 201 may be advanced while maintaining the outer steerable catheter 202, the inner steerable catheter 203, and the inner compression shaft 205 in a stationary position. In another example, the outer steerable catheter 202, the inner steerable catheter 203, and the inner compression shaft 205 may be retracted while the introducer sheath 201 is advanced. As the brim recapture funnel 204 is pulled into the introducer sheath 201, the force of the introducer sheath 201 applies a longitudinal force directed distally to the brim recapture funnel 204, which causes the brim recapture funnel 204 to collapse around the valve brim 104 and capture the valve brim 104.

Figure 7D:
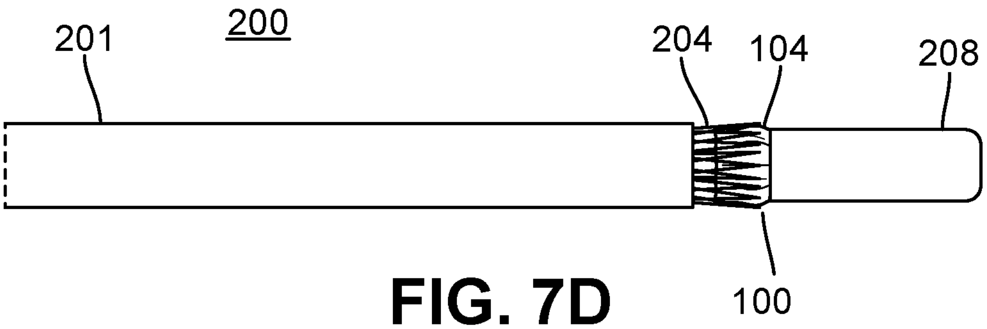

FIG. 7D illustrates the brim recapture funnel 204 further collapsing around the valve brim 104 to capture the valve brim 104. The outer steerable catheter 202, the inner steerable catheter 203, and the inner compression shaft 205 are further drawn back together into the introducer sheath 201 to continue the capture of the valve brim 104.

Figure 7E:
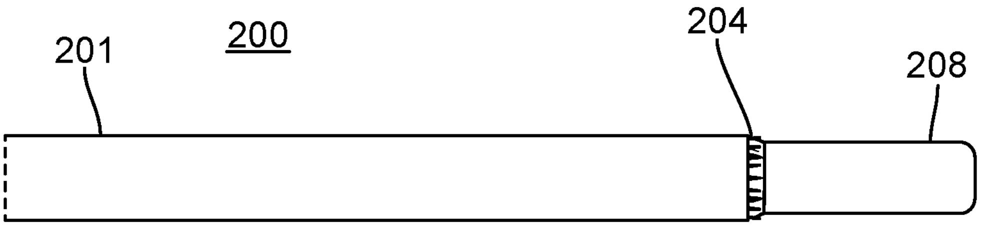

FIG. 7E illustrates the brim recapture funnel 204 completing the collapse around the valve brim 104 to capture the valve brim 104. The outer steerable catheter 202, the inner steerable catheter 203, and the inner compression shaft 205 are further drawn back together into the introducer sheath 201 to complete the capture of the valve brim 104.

Figure 7F:
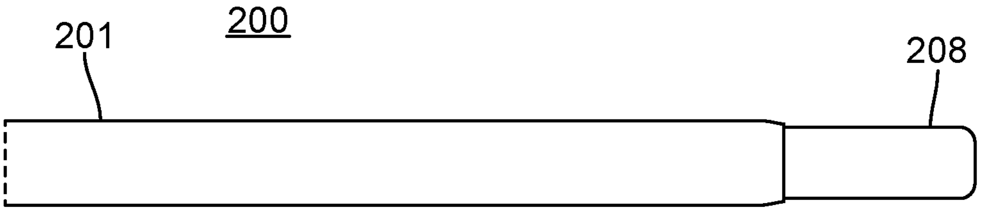

FIG. 7F illustrates the recapture delivery catheter 200 after the valve brim 104 has been fully captured. The valve brim 104 has been fully withdrawn into the introducer sheath 201. In this configuration, wherein the valve brim 104 is completely within the introducer sheath 201, the introducer sheath 201 may pull the prosthetic heart valve 100 back across the septum of the patient for withdrawal without injury to patient anatomy.

Figure 8:
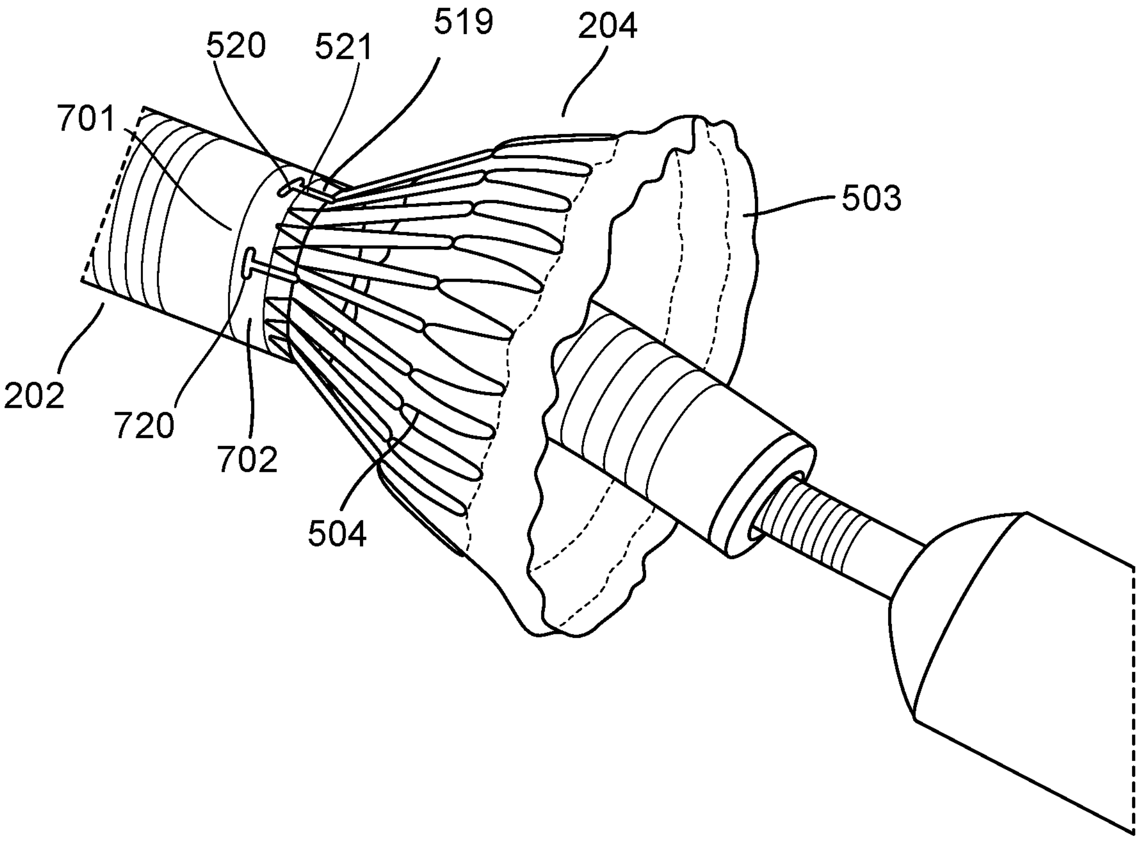
FIG. 8 illustrates a closeup view of a connection between a brim recapture funnel and a recapture delivery catheter according to embodiments hereof.

FIG. 8 illustrates a close-up view of a connection between a brim recapture funnel and a recapture delivery catheter according to embodiments hereof. The brim recapture funnel 204 is connected to the outer steerable catheter 202 via the mounting paddles 519. The mounting paddles 519 mate with and are mechanically jailed by mounting slots 720. The mounting slots 720 are slots in a distal termination portion 701 of the outer steerable catheter 202. The distal termination portion 701 of the outer steerable catheter 202 is the distalmost portion of the outer steerable catheter 202. The mounting slots 720 are sized and shaped to accommodate the mounting paddles 519 inserted therein. When the mounting paddles are inserted into the mounting slots 720, lateral movement of the brim recapture funnel 204 is prevented. The distal termination portion 701 of the outer steerable catheter 202 may further include a collar 702 configured to secure the mounting paddles 519 within the mounting slots 720.

The mounting configuration described above may be beneficial when using nitinol as a material for the brim recapture funnel 24. Nitinol bonds poorly to steel when welded and the mechanical connection offered by the mounting slots 720, collar 702, and mounting paddles 519 serve to secure the brim recapture funnel 204 to the outer steerable catheter 202 where a welded connection may not provide a secure connection. In embodiments wherein the brim recapture funnel 204 is constructed of differing materials that may bond more securely with a material of the outer steerable catheter 202 (for example, where the outer steerable catheter 202 and the brim recapture funnel are both constructed of steel) the brim recapture funnel 204 may be secured to the outer steerable catheter 202 via welding or other bonding technique.

Figure 9:
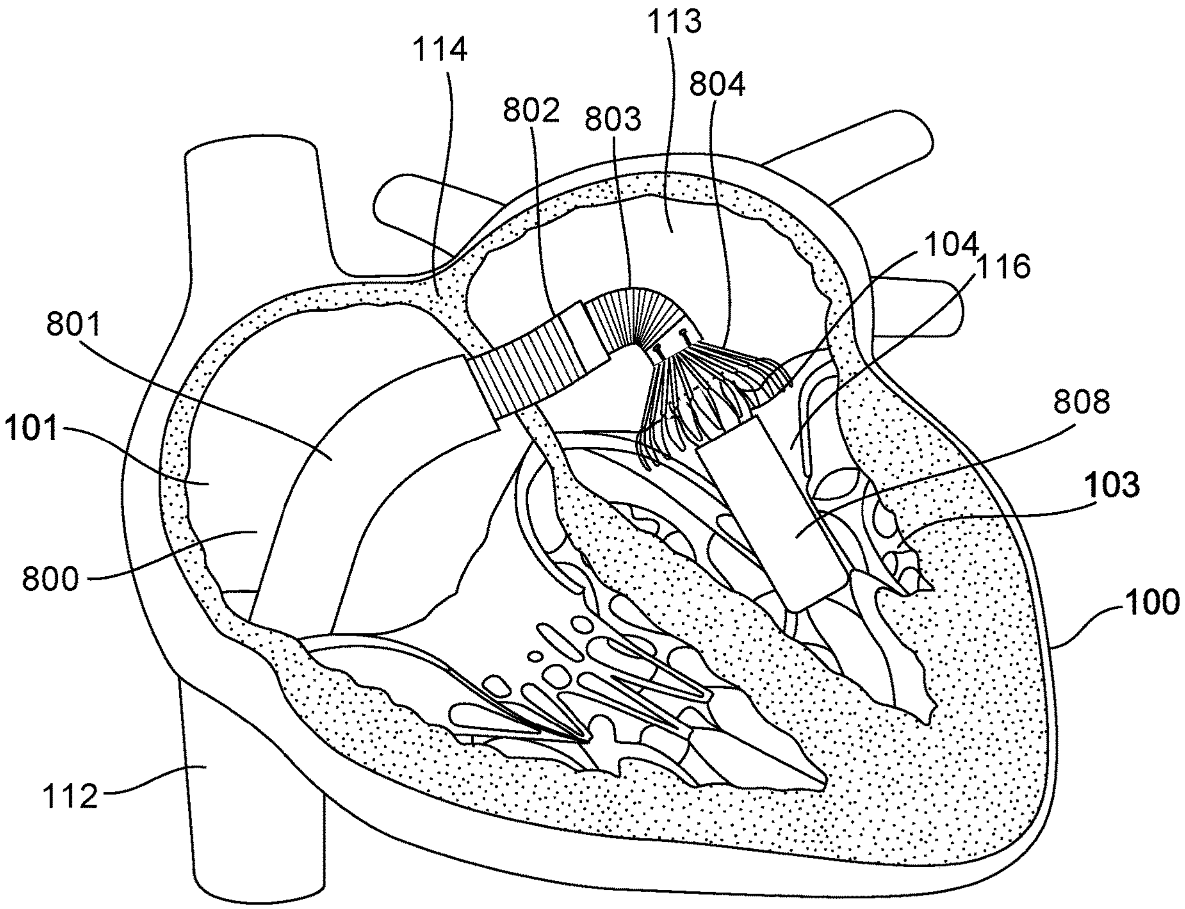
FIG. 9 is an in situ illustration of a delivery catheter including a brim recapture funnel according to embodiments hereof.

FIG. 9 is an in situ illustration of a recapture delivery catheter 800 including a brim recapture funnel 804 being used to deliver a prosthetic heart valve to a mitral valve site according to embodiments hereof. The recapture delivery catheter 800 includes an outer steerable catheter 802, an inner steerable catheter 803, the brim recapture funnel 804, an inner compression shaft 805 (not shown in FIG. 9), and a distal sheath capsule 808. The brim recapture funnel 804 is located at a distal end of the inner steerable catheter 803. Disposed within the distal sheath capsule 808 during delivery is the prosthetic heart valve 100 having a valve brim 104 protruding proximally from the distal sheath capsule 808. As shown in FIG. 9, the recapture delivery catheter 800 may be delivered to the deployment site via an introducer sheath 801. The introducer sheath 801 is tracked to the right atrium 101 via the inferior vena cava 112. The introducer sheath 801 may be used to make a transeptal entry into the left atrium 113 across the septum 114. In embodiments, the introducer sheath 801 may be retracted across the septum 114 after the distal sheath capsule 808, the inner steerable catheter 803, and the outer steerable catheter 802 have crossed the septum 114. The prosthetic heart valve 100 may be delivered to a mitral valve site 116. Although illustrated with respect to a mitral valve replacement delivery, embodiments of recapture delivery catheters as disclosed herein may be used for any type of valve deployment and recapture.

Figure 10:
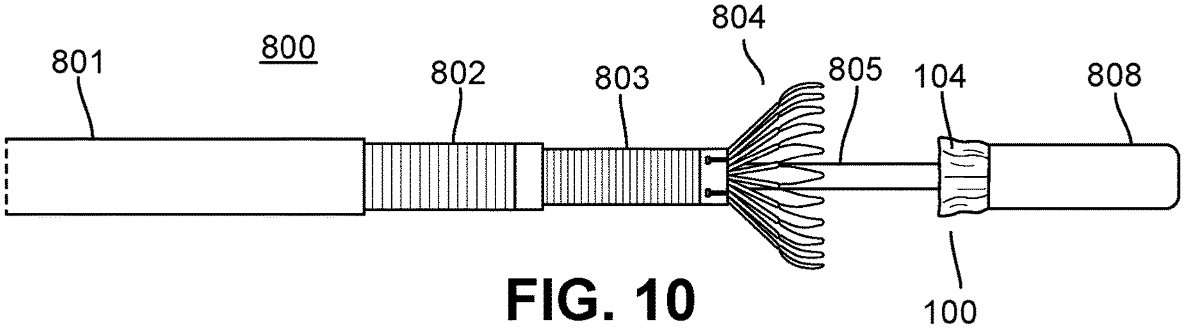
FIG. 10 illustrates a recapture delivery catheter including a brim recapture funnel according to embodiments hereof.

FIG. 10 illustrates a recapture delivery catheter including a brim recapture funnel according to embodiments hereof. As discussed above, the recapture delivery catheter 800 includes an outer steerable catheter 802, an inner steerable catheter 803, a brim recapture funnel 804, an inner compression shaft 805, and a distal sheath capsule 808. The brim recapture funnel 804 is located at the distal end of the inner steerable catheter 803. The brim recapture funnel 804 shares features with the brim recapture funnel 204, as discussed above with respect to FIGS. 3A-3C. The recapture delivery catheter 800 may be delivered to a deployment site via an introducer sheath 801. The outer steerable catheter 802 is a flexible catheter shaft and may be made of any suitable materials, including stainless steel, polymers, etc. The outer steerable catheter 802 is connected to a recapture delivery catheter handle (not shown) and may be steered and/or actuated via controls built into the handle. The inner steerable catheter 803 is a flexible catheter shaft and may be made of any suitable materials, including stainless steel, polymers, etc. The inner steerable catheter 803 is connected to a recapture delivery catheter handle (not shown) and may be steered and/or actuated via controls built into the handle. The inner compression shaft 805 is connected to the distal sheath capsule 808. The distal sheath capsule 808 houses the prosthetic heart valve 100 such that the valve brim 104 protrudes proximally. The inner compression shaft 805 and distal sheath capsule 808 together house a hydraulic deployment system (not shown) that is configured to cause proximal and distal translation of the distal sheath capsule 808 with respect to the prosthetic heart valve 100 for deployment. Thus, activation of the hydraulic system may push the distal sheath capsule 808 distally to expose and deploy the prosthetic heart valve 100 and may pull the distal sheath capsule 808 proximally to cover and retract the prosthetic heart valve 100.

The configuration shown in FIG. 10 is an operational configuration. During valve delivery and deployment, the inner steerable catheter 803 and the outer steerable catheter 802 are manipulated and steered, via the handle controls, to align the distal sheath capsule 808 housing the prosthetic heart valve 100 with a proper deployment position. The inner compression shaft 805 is used to extend the distal sheath capsule 808 away from the inner steerable catheter 803 and into a proper deployment position. In this configuration, the brim recapture funnel 804 is in an open or extended configuration and is ready to perform a brim recapture should it become necessary.

Figure 11:
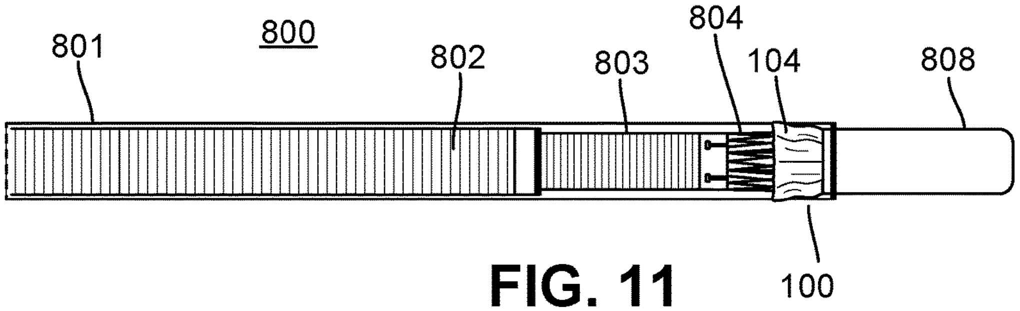
FIG. 11 illustrates a recapture delivery catheter including a brim recapture funnel configured for deployment according to embodiments hereof.

FIG. 11 illustrates the recapture delivery catheter 800 including the brim recapture funnel 804 in a first delivery configuration according to embodiments hereof. In this first delivery configuration, the recapture delivery catheter 800 is configured for safe delivery through the introducer sheath, across the septum, and into the left atrium. In the delivery configuration, the brim recapture funnel 804 is folded or collapsed and tucked underneath the valve brim 104. The brim recapture funnel 804 is a collapsible funnel and is configured to rest in an open configuration. When collapsed and tucked underneath the valve brim 104, the brim recapture funnel 804 is maintained in a closed state by force from the valve brim 104 which is, in turn, maintained in a closed state by the introducer sheath 801. During deployment of the prosthetic heart valve 100, the brim recapture funnel 804 may be released from the valve brim 104 by advancing the inner compression shaft 805 (and the prosthetic heart valve 100 with it) distally with respect to the brim recapture funnel 804.

Figure 12A:
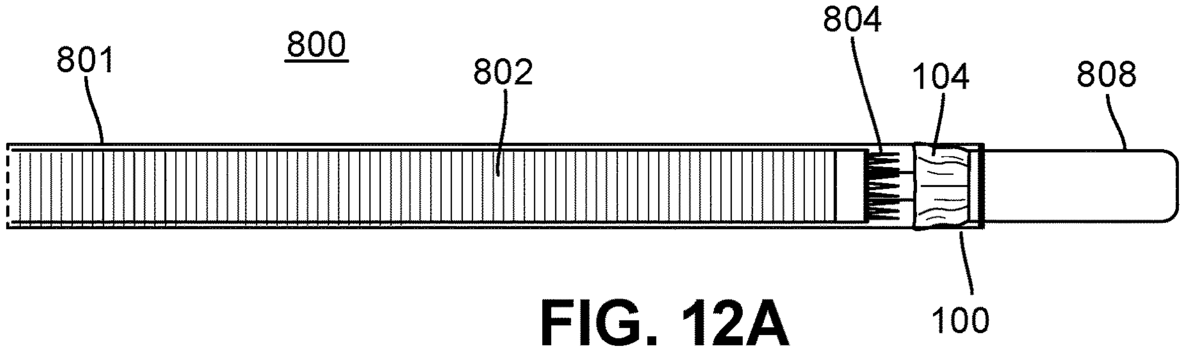
FIG. 12A illustrates a recapture delivery catheter including a brim recapture funnel configured for deployment according to embodiments hereof.

FIG. 12A illustrates the recapture delivery catheter 800 including the brim recapture funnel 804 in an alternate delivery configuration according to embodiments hereof. In this alternate delivery configuration, the recapture delivery catheter 800 is configured for safe delivery through the introducer sheath, across the septum, and into the left atrium. In the alternate delivery configuration, the brim recapture funnel 804 is folded or collapsed and pulled completely or partially into the outer steerable catheter 802. The brim recapture funnel 804 is collapsed and maintained in a closed state by force from the outer steerable catheter 802. In embodiments, the brim recapture funnel 804 may be pulled completely into the outer steerable catheter 802 such that no portion protrudes from a distal end of the outer steerable catheter 802. In further embodiments, the brim recapture funnel 804 may be pulled partially into the outer steerable catheter 802 such that a portion protrudes from a distal end of the outer steerable catheter 802. During delivery and deployment of the prosthetic heart valve 100, the brim recapture funnel 804 may be released, as necessary, by advancing the inner steerable catheter 803 (and the brim recapture funnel 804 with it) distally with respect to the outer steerable catheter 802.

Figure 12B:
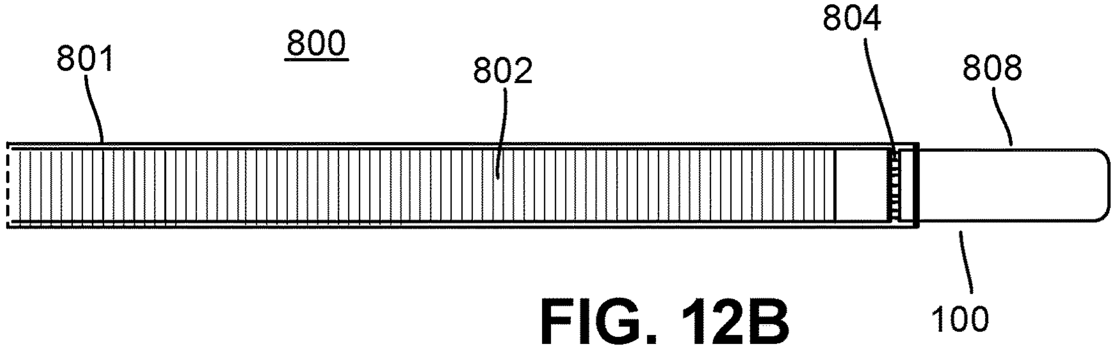
FIG. 12B illustrates a recapture delivery catheter including a brim recapture funnel configured for deployment according to embodiments hereof.

FIG. 12B illustrates the recapture delivery catheter 800 including the brim recapture funnel 804 in an alternate delivery configuration according to embodiments hereof. In this alternate delivery configuration, the recapture delivery catheter 800 is configured for safe delivery through the introducer sheath, across the septum, and into the left atrium. In the alternate delivery configuration, the brim recapture funnel 804 is folded or collapsed over the valve brim of the prosthetic heart valve (not shown). Both the brim recapture funnel 804 and the valve brim of the prosthetic hear valve (not shown) are withdrawn into the outer steerable catheter 802. The brim recapture funnel 804 is collapsed and maintained in a closed state by force from the outer steerable catheter 802. In embodiments, the brim recapture funnel 804 and the valve brim may be pulled completely into the outer steerable catheter 802 such that no portion protrudes from a distal end of the outer steerable catheter 802. In further embodiments, the brim recapture funnel 804 and valve brim may be pulled partially into the outer steerable catheter 802 such that a portion protrudes from a distal end of the outer steerable catheter 802 (e.g., as shown in FIG. 12B). During delivery and deployment of the prosthetic heart valve 100, the brim recapture funnel 804 may be released, as necessary, by advancing the inner steerable catheter 803 (and the brim recapture funnel 804 with it) distally with respect to the outer steerable catheter 802.

The delivery configurations described above of the recapture delivery catheter 800 are configured to facilitate the advancement of the distal sheath capsule 808. As the recapture delivery catheter 800 is advanced distally through an introducer sheath the forces on the distal sheath capsule 808 and the valve brim 104 are directed proximally. In the delivery configuration described with respect to FIG. 11, forces in the proximal direction tend to encourage the valve brim 104 to remain unexpanded and to maintain pressure on the brim recapture funnel 804. In the alternate delivery configurations described with respect to FIG. 12A and FIG. 12B, the contraction of the brim recapture funnel 804 is maintained by the outer steerable catheter 802 such that the distal ends of the brim recapture funnel 804 are maintained at a diameter small enough such that they do not interfere with the advancement of the recapture delivery catheter 800. During deployment, when the inner steerable catheter 803 is advanced away from outer steerable catheter 802 the brim recapture funnel 804 is freed to expand into the open resting position, as illustrated in FIG. 10.

FIGS. 13A-13D illustrate stages in a valve recapture operation using a recapture delivery catheter according to embodiments hereof. When the distal sheath capsule 808 is advanced away from the brim recapture funnel 804, the brim recapture funnel 804 expands into the open configuration shown in FIG. 13A.

Figure 13A:
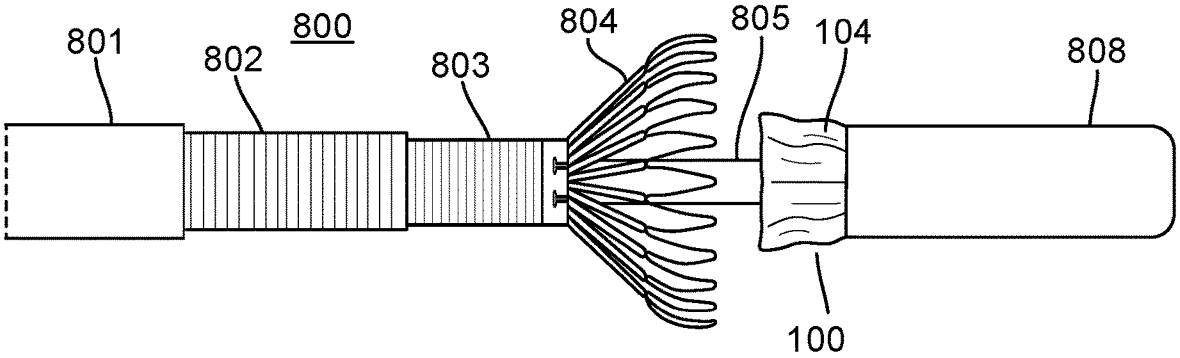
FIGS. 13A-13D illustrate stages in a valve recapture operation using a recapture delivery catheter according to embodiments hereof.
Figure 13B:
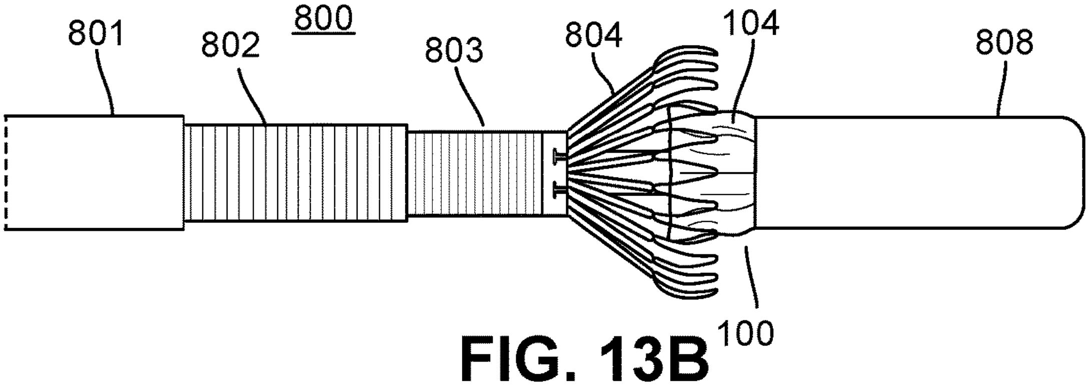

After a failed valve deployment, the inner compression shaft 805 and associated hydraulic system is used to draw the prosthetic heart valve 100 back into the distal sheath capsule 808 as far as possible. The valve brim 104 continues to protrude proximally from the distal sheath capsule 808. To ensure that the valve brim 104 can be drawn back across the septum without damage to the patient anatomy, the brim recapture funnel 804 is used to capture the valve brim 104. FIG. 13B illustrates the valve brim 104 inside the recapture field of the brim recapture funnel 804 and the beginning of contraction of the brim recapture funnel 804. After the valve brim 104 has been brought inside the recapture field of the brim recapture funnel 804, the inner steerable catheter 803, and the inner compression shaft 805 are drawn back together into the outer steerable catheter 802. As the brim recapture funnel 804 is pulled into the outer steerable catheter 802, the outer steerable catheter 802 applies a longitudinal force directed distally to the brim recapture funnel 804, which causes the brim recapture funnel 804 to collapse around the valve brim 104 and capture the valve brim 104.

Figure 13C:
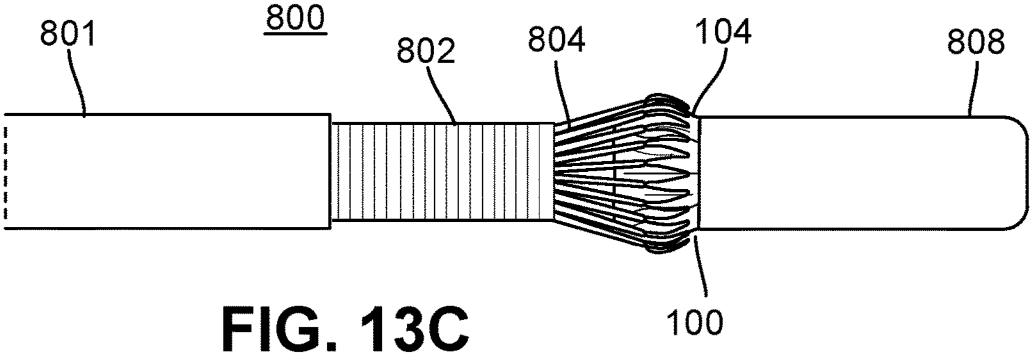

FIG. 13C illustrates the brim recapture funnel 804 further collapsing around the valve brim 104 to capture the valve brim 104. The inner steerable catheter 803 and the inner compression shaft 805 are further drawn back together into the outer steerable catheter 802 to continue the capture of the valve brim 104 through radial pressure on the brim recapture funnel 804.

Figure 13D:
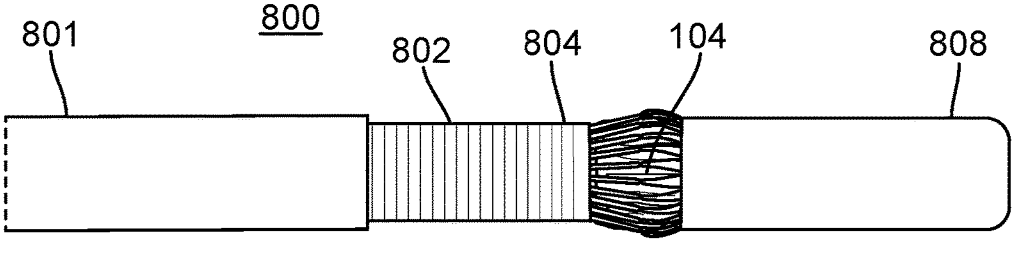

FIG. 13D illustrates the brim recapture funnel 804 after completion of valve brim 104 capture. Completion of capture occurs when the brim recapture funnel 804 is drawn back into the outer steerable catheter 802 far enough to create sufficient force on the valve brim 104 to maintain capture during a recovery operation to withdraw the recapture delivery catheter 800 from the patient. Completion of capture may include withdrawing the brim recapture funnel 804 completely into the outer steerable catheter 802 and/or partially into the outer steerable catheter 802, as illustrated in FIG. 13D. It is not necessary for the valve brim 104 to be drawn completely into the outer steerable catheter 802 for capture to be complete. The tapered shape of the brim recapture funnel 804 acts to prevent the valve brim 104 from catching on or damaging patient anatomy as the recapture delivery catheter 800 is withdrawn.

In embodiments, the recapture delivery catheter 800 may be withdrawn into the introducer sheath to 801 to pull the prosthetic heart valve 100 back across the septum of the patient for withdrawal without injury. In alternate embodiments, the prosthetic heart valve 100 may be pulled back across the septum prior to withdrawal into the introducer sheath to 801.

Figure 14:
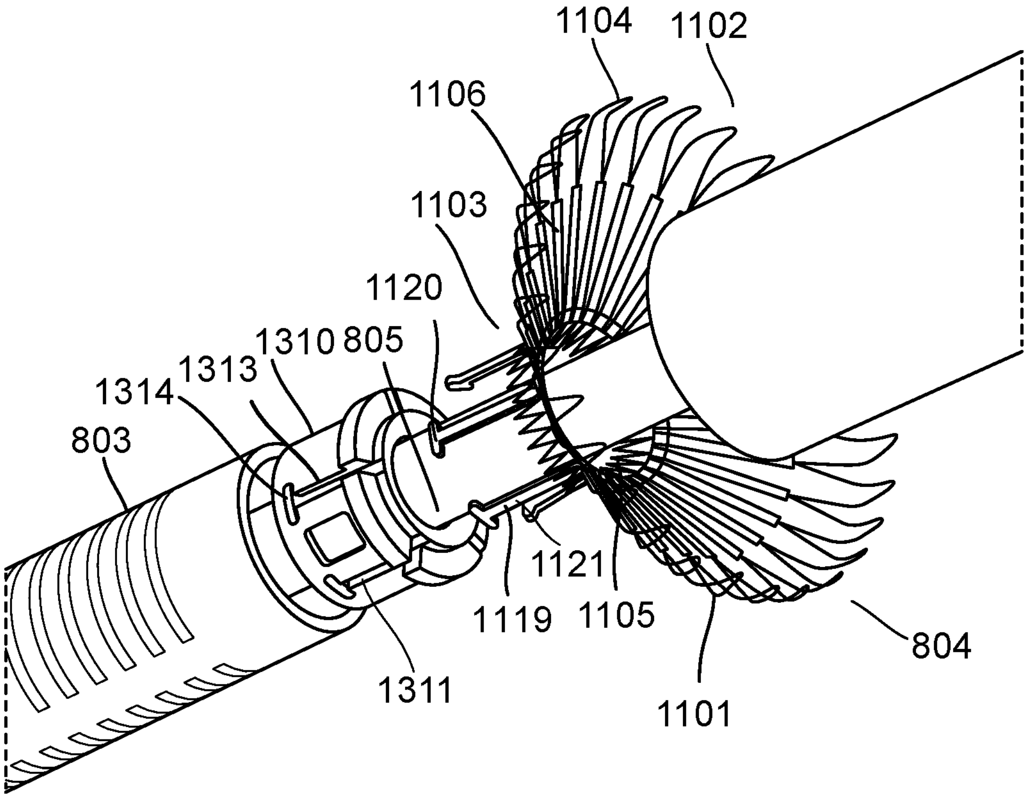
FIG. 14 illustrates a close-up view of a connection between a brim recapture funnel and a recapture delivery catheter according to embodiments hereof.

FIG. 14 illustrates a close-up view of a connection between a brim recapture funnel and a recapture delivery catheter according to embodiments hereof. The brim recapture funnel 804 is constructed similarly to the brim recapture funnel 204, as illustrated in FIG. 3A, and includes all of the same elements. The brim recapture funnel 804 includes a frame 1101. The frame 1101 has a distal end 1102 and a proximal end 1103 and is divided into three portions. The frame 1101 includes a distal contraction section 1104 located at the distal end 1102, a proximal contraction section 1105 located at the proximal end 1103, and a midsection 1106 located therebetween. The brim recapture funnel 804 further includes one or more mounting paddles 1119. The one or more mounting paddles 1119 are integrally connected to the frame 1101, for example at the proximal contraction section 1105 or the midsection 1106. The mounting paddles 1119 are T-shaped members that extend proximally from the frame 1101. The mounting paddles 1119 include a paddle portion 1120 and an extension portion 1121. A distal end of the extension portion 1121 is connected to the frame 1101 and a proximal end of the extension portion 1121 is connected to the paddle portion 1120. The paddle portion 1120 is wider than the extension portion 1121 and may be rectangular, square, circular, oval, and/or any other suitable shape.

The brim recapture funnel 804 differs from the brim recapture funnel 204 chiefly in the positioning of one or more mounting paddles 1119. The mounting paddles 1119 of the brim recapture funnel 804 are connected to frame 1101 of the brim recapture funnel 804 in a location that permits mechanical interlock with a compression shaft collar 1310. The compression shaft collar 1310 is a collar disposed over the inner compression shaft 805 and sized to fit within the distal end of the inner steerable catheter 803. The compression shaft collar 1310 is slidably disposed over the inner compression shaft 805. The compression shaft collar 1310 includes one or more mounting slots 1311. The mounting slots 1311 are sized and shaped to conform to the mounting paddles 1119 and have an elongated portion 1313 sized and shaped to accommodate the extension portion 1121 and a cross portion 1314 sized and shaped to accommodate the paddle portion 1120. The cross portion 1314 extends orthogonally to the elongated portion 1313 such that the cross portion 1314 is wider in a circumferential dimension than the elongated portion 1313. This arrangement permits a mechanical lock-in or jailing effect to maintain the position of the brim recapture funnel 804. As discussed above, the brim recapture funnel 804 may be manufactured of nitinol and may therefore be difficult or impossible to reliably weld to the remaining stainless steel parts of the inner steerable catheter 803. When the brim recapture funnel 804 is locked in place by the mechanical connection between the mounting paddles 1319 and the mounting slots 1311, the compression shaft collar 1310 is inserted into the distal end of the inner steerable catheter 803. The compression shaft collar 1310 may be welded in place to the inner steerable catheter 803 and/or secured via alternative mechanical means. With the compression shaft collar 1310 positioned inside the distal end of the inner steerable catheter 803, the brim recapture funnel 804 is secured to the inner steerable catheter 803.

FIGS. 15A-D illustrate stages of a prosthetic heart valve recapture operation with respect to patient anatomy using a recapture delivery catheter according to embodiments hereof. FIGS. 15A-D are illustrated with respect to the recapture delivery catheter 200 having the brim recapture funnel 204 located on the outer steerable catheter 202. All stages of recapture illustrated in FIGS. 15A-D may also be carried out with the recapture delivery catheter 800 having the brim recapture funnel 804 located on the inner steerable catheter 803. FIGS. 15A-15D illustrate relative positions, with respect to the patient septum 114, of the various components of the recapture delivery catheter 200 during a recapture operation.

Figure 15A:
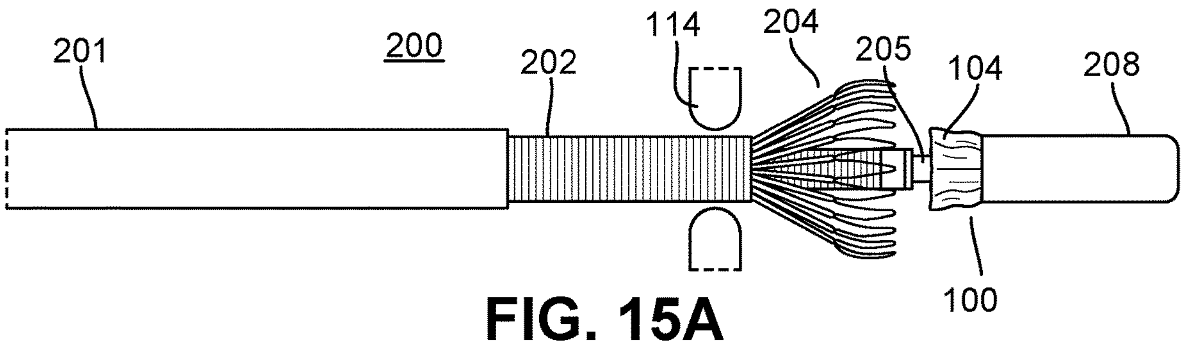
FIGS. 15A-15D illustrate stages of a valve recapture operation using a recapture delivery catheter according to embodiments hereof.

FIG. 15A illustrates relative positions of the introducer sheath 201, the outer steerable catheter 202, the inner steerable catheter 203, the brim recapture funnel 204, the inner compression shaft 205, and the distal sheath capsule 208 during a deployment operation. The introducer sheath 201 has been withdrawn across the septum 114 to the right atrium, although in some embodiments the introducer sheath 201 may remain in the left atrium. The outer steerable catheter 202 extends into the left atrium and the brim recapture funnel 204 is in an open configuration. The inner steerable catheter 203 and inner compression shaft 205 extend away from the outer steerable catheter 202. The distal sheath capsule 208 houses the prosthetic heart valve 100, with the valve brim 104 extending proximally from a proximal end of the distal sheath capsule 208.

Figure 15B:
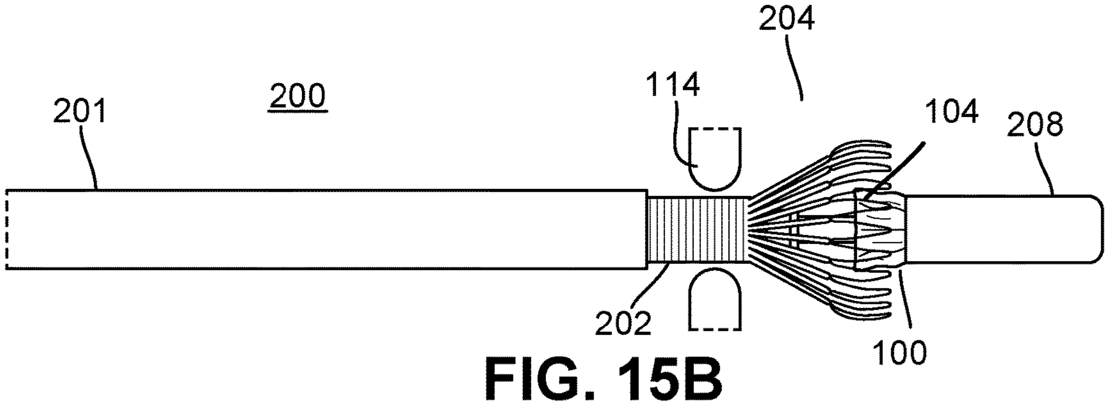

FIG. 15B illustrates an initial stage of a recapture operation. After it has been determined that recapture is necessary, e.g., due to failed valve deployment, the recapture operation begins. The prosthetic heart valve 100 is brought back into the distal sheath capsule 208 as far as it is able through operation of the hydraulic system of the inner compression shaft 205. The inner compression shaft 205 and the inner steerable catheter 203 are then pulled back towards to the outer steerable catheter 202.

Figure 15C:
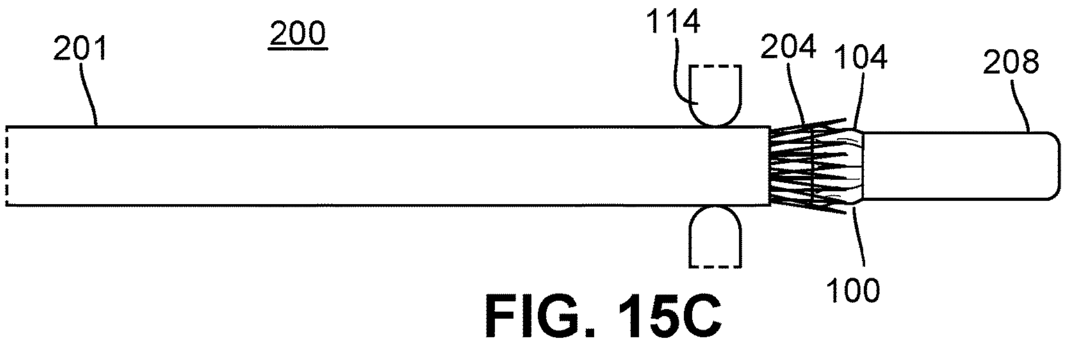
Figure 15D:
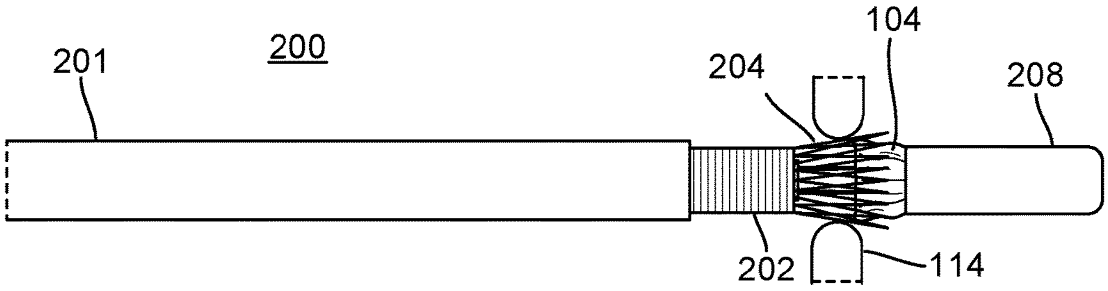

FIG. 15C and FIG. 15D illustrate alternative operations in a recapture delivery operation. In a first alternative recapture operation, as shown in FIG. 15C, the introducer sheath 201 is advanced across the septum 114 into the left atrium (or left to remain there if already in position). The outer steerable catheter 202 is withdrawn into the introducer sheath 201, thereby causing the brim recapture funnel 204 to contract and capture the valve brim 104. Once captured, the outer steerable catheter 202 may be withdrawn further into the sheath or remain partially withdrawn into the sheath as the prosthetic heart valve 100 and distal sheath capsule 208 are pulled across the septum, into the right atrium, and out of the patient.

FIG. 15D illustrates an alternate embodiment in which the introducer sheath 201 is not advanced across the septum 114. Instead, pressure from the septum 114 is used to provide pressure or force to the brim recapture funnel 204 to close and/or maintain closure of the brim recapture funnel 204 over the valve brim 104 while the prosthetic heart valve 100 and distal sheath capsule 208 are drawn back across the septum 114. After withdrawal across the septum 114, the brim recapture funnel 204 may be pulled back into the introducer sheath 201 or may be left out of the introducer sheath 201 before removal from the patient.

FIGS. 16A-D illustrate stages of a prosthetic heart valve recapture operation with respect to patient anatomy using a recapture delivery catheter according to embodiments hereof. FIGS. 16A-D are illustrated with respect to the recapture delivery catheter 800 having the brim recapture funnel 804 couple to the inner steerable catheter 803. FIGS. 16A-D illustrate relative positions, with respect to the patient septum 114, of the various components of the recapture delivery catheter 800 during a recapture operation.

Figure 16A:
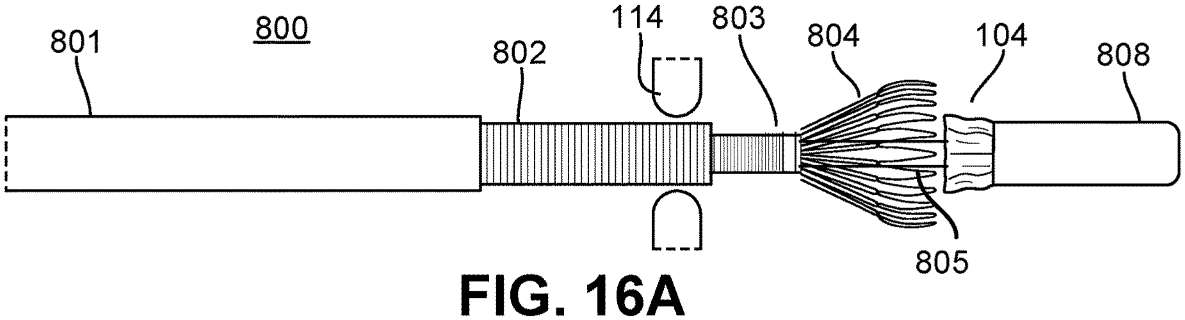
FIG. 16A-16D illustrates a recapture delivery catheter used to maintain a transeptal entry according to embodiments hereof.

FIG. 16A illustrates relative positions of the introducer sheath 201, the outer steerable catheter 802, the inner steerable catheter 803, the brim recapture funnel 804, the inner compression shaft 805, and the distal sheath capsule 808 during a deployment operation. The introducer sheath 201 has been withdrawn across the septum 114 to the right atrium, although in some embodiments the introducer sheath 201 may remain in the left atrium. The outer steerable catheter 802 extends into the left atrium and the brim recapture funnel 804 is in an open configuration. The inner steerable catheter 803 and inner compression shaft 805 extend away from the outer steerable catheter 802. The distal sheath capsule 808 houses the prosthetic heart valve 100, with the valve brim 104 thereof extending proximally from the distal sheath capsule 808.

Figure 16B:
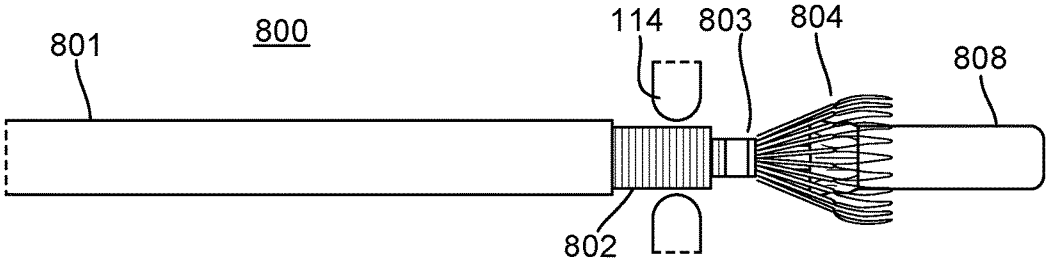

FIG. 16B illustrates an initial stage of a recapture operation. After it has been determined that recapture is necessary, e.g., due to failed valve deployment, the recapture operation begins. The prosthetic heart valve 100 is brought back into the distal sheath capsule 808 as far as it is able through operation of the hydraulic system of the inner compression shaft 805. The inner compression shaft 805 is then pulled back towards the inner steerable catheter 803.

Figure 16C:
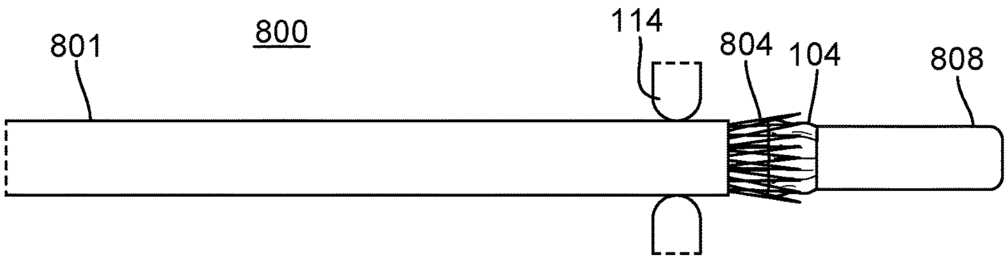
Figure 16D:
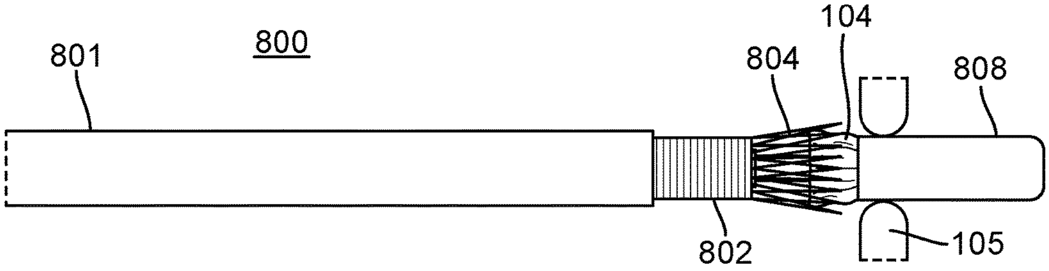

FIG. 16C and FIG. 16D illustrate alternative operations in a recapture delivery operation. In a first alternative recapture operation, as shown in FIG. 16C, the introducer sheath 201 is advanced across the septum 114 into the left atrium (or left to remain there if already in position). The inner steerable catheter 803 is withdrawn into the outer steerable catheter 802 thereby causing the brim recapture funnel 204 to contract and capture the valve brim 104. Once the valve brim 104 is captured, the outer steerable catheter 202 and the inner steerable catheter 803 are then withdrawn together into the introducer sheath 201 or remain partially withdrawn into the sheath as the prosthetic heart valve 100 and distal sheath capsule 208 are pulled across the septum, into the right atrium, and out of the patient.

FIG. 16D illustrates an alternate embodiment in which the introducer sheath 201 is not advanced across the septum 114. Instead, the valve brim 104 is captured via closure of the brim recapture funnel 804 during withdrawal of the brim recapture funnel 804 into the outer steerable catheter 802. After capture, the outer steerable catheter 802, the outer steerable catheter 802, the inner steerable catheter 803, the brim recapture funnel 804, and the distal sheath capsule 808 (containing the prosthetic heart valve 100) are withdrawn together across the septum 114. After withdrawal across the septum 114, the outer steerable catheter 802, the inner steerable catheter 803, the brim recapture funnel 804, and the distal sheath capsule 808 (containing the prosthetic heart valve 100) are withdrawn into the introducer sheath 201 before removal from the patient.

Figure 17:
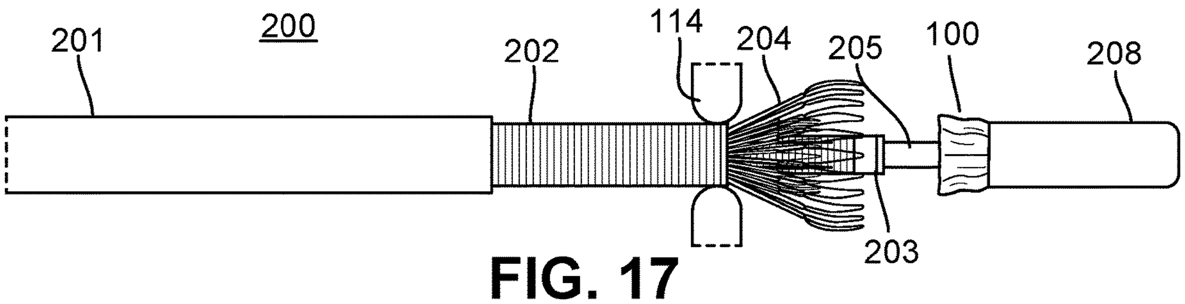
FIG. 17 illustrates recovery of an empty distal sheath capsule with a recapture delivery catheter according to embodiments hereof.

FIG. 17 illustrates a recapture delivery catheter used to maintain a transeptal entry according to embodiments hereof. The recapture delivery catheter 200, having the brim recapture funnel 204 located on the outer steerable catheter 202, may be used to maintain transeptal entry. After gaining left atrium access across the septum 114, the inner compression shaft 205 is used to begin deployment of the prosthetic heart valve 100. The brim recapture funnel 204 is released and opens to its open configuration. In the open configuration, the brim recapture funnel 204 acts to hold the position of the outer steerable catheter. Although force applied in a proximal direction to the recapture delivery catheter 200 may cause the brim recapture funnel 204 to contract and pull back across the septum 114, the force required is greater than that required without the brim recapture funnel 204. Thus, the brim recapture funnel 204 acts to maintain the transeptal crossing, particularly with respect to small and non-deliberate forces that may occur while the various elements of the recapture delivery catheter 200 are manipulated to deploy the prosthetic heart valve 100.

Figure 18A:
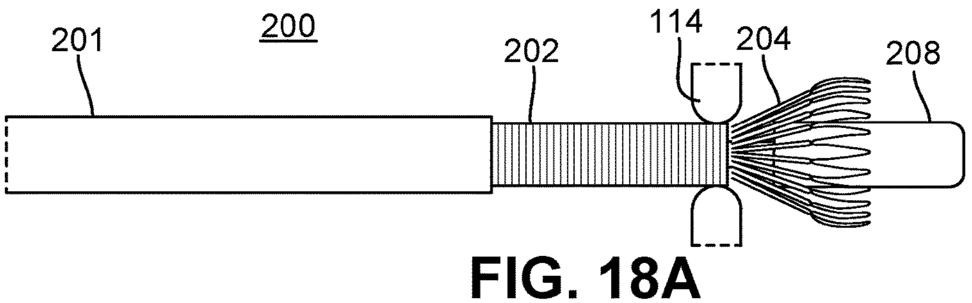
FIGS. 18A-18B illustrate recovery of an empty distal sheath capsule with a recapture delivery catheter according to embodiments hereof.
Figure 18B:
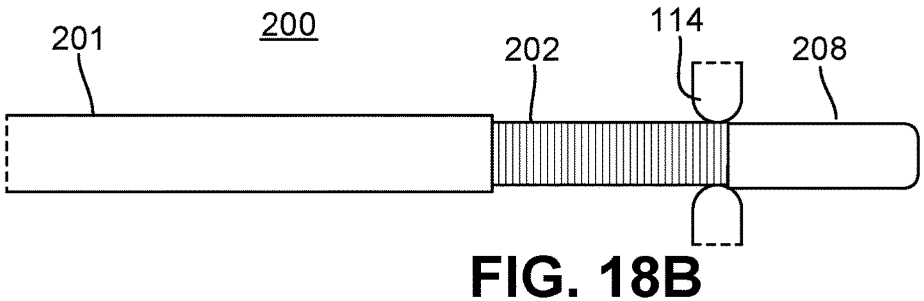

FIGS. 18A-18B illustrate recovery of an empty distal sheath capsule with a recapture delivery catheter according to embodiments hereof.

FIG. 18A illustrates recovery of the distal sheath capsule 208 by the recapture delivery catheter 200, in an embodiment. Capturing the distal sheath capsule 208 prior to removal may prevent edges or corners of the distal sheath capsule 208 from catching on the septum 114 as it is withdrawn, particularly the proximal edge of the distal sheath capsule 208. The brim recapture funnel 204 may be used to capture the edges of the distal sheath capsule 208 in fashion similar to that described above with respect to the valve brim 104 capture. After capture, the distal sheath capsule 208 may be withdrawn across the septum 114, either in the introducer sheath 201 or outside of the introducer sheath 201.

FIG. 18B illustrates recovery of the distal sheath capsule 208 by the recapture delivery catheter 200, in an embodiment. Capturing the distal sheath capsule 208 prior to removal may prevent edges or corners of the distal sheath capsule 208 from catching on the septum 114 as it is withdrawn, particularly the proximal edge of the distal sheath capsule 208. The brim recapture funnel 204 (not shown) may be captured inside of the distal sheath capsule 208, which may be retracted to also cover the inner steerable catheter 203. The distal sheath capsule 208 may be further retracted until its proximal edge is disposed inside of the outer steerable catheter 204, as shown in FIG. 18B. After capture, the distal sheath capsule 208 may be withdrawn across the septum 114, either in the introducer sheath 201 or outside of the introducer sheath 201.

In further embodiments, "capturing" the distal sheath capsule 208 is not required provided that the brim capture funnel 204 extends over the proximal opening of the distal sheath capsule 208. In such an embodiment, any tissue encountered while proximally retracting the recapture delivery catheter 200 will act on the brim capture funnel 204 rather than the edge of the proximal opening of the distal capsule sheath.

As discussed above with respect to FIG. 1, the prosthetic heart valve 100 incudes a flexible valve brim hinge 106. The valve brim hinge 106 permits the valve brim 104 to flex and/or hinge with respect to the stent 102 of the prosthetic heart valve 100. In particular, the valve brim hinge 106 permits the valve brim 104 to fold back or invert completely with respect to the stent 102 such that the valve brim 104 extends distally from the valve brim hinge 106, rather than proximally as in a standard configuration. This feature may be used in various recovery techniques to improve valve recapture.

Figure 19A:
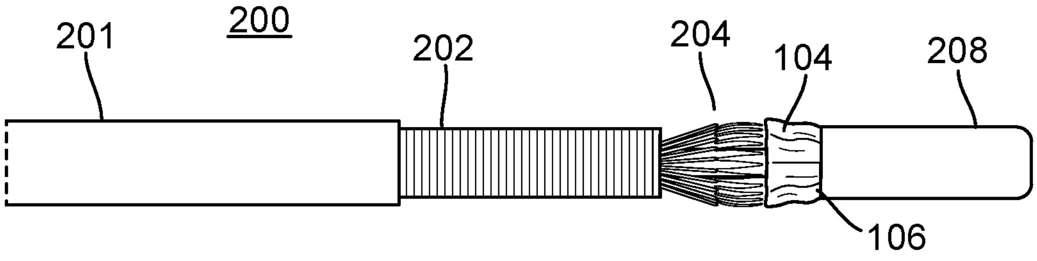
FIG. 19A-19C illustrate stages in a valve recapture operation using a recapture delivery catheter according to embodiments hereof.
Figure 19B:
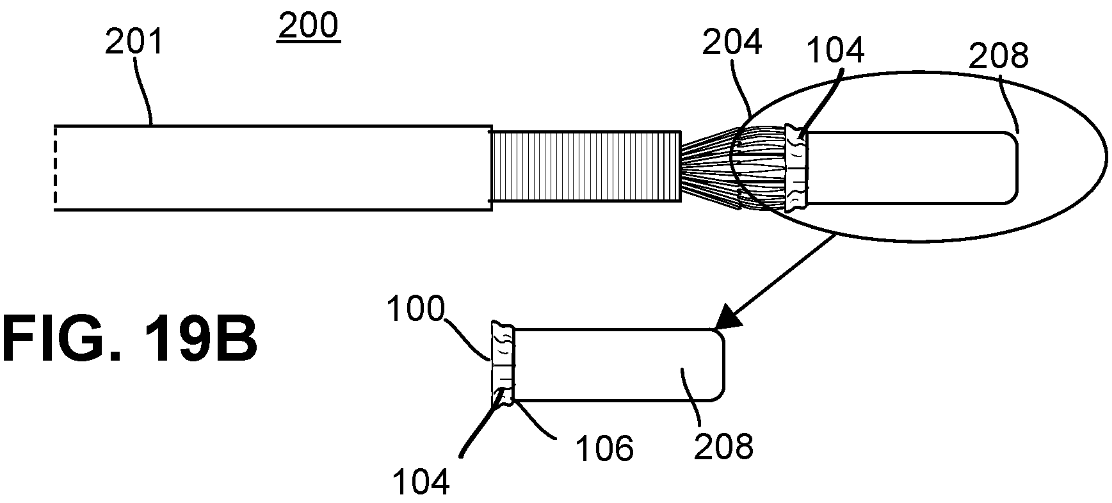
Figure 19C:
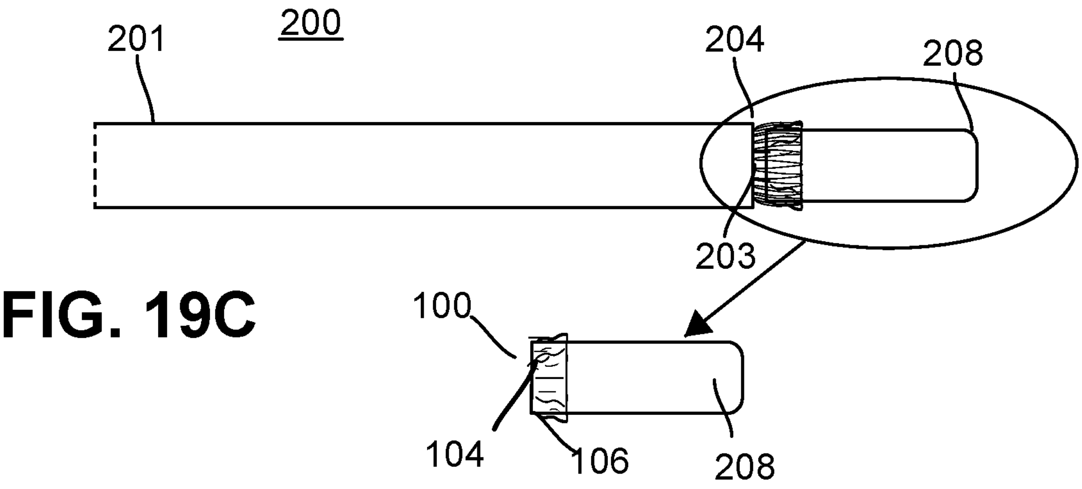

FIGS. 19A-19C illustrate the use of recapture delivery catheter 200 in a valve brim inversion technique for recapturing the prosthetic heart valve 100. As discussed above, the recapture delivery catheter 200 includes an outer steerable catheter 202, an inner steerable catheter 203 (e.g., as shown in FIG. 5), a brim recapture funnel 204, an inner compression shaft 205 (e.g., as shown in FIG. 5), and a distal sheath capsule 208. The brim recapture funnel 204 is coupled to the outer steerable catheter 202. The prosthetic heart valve 100 is disposed within the distal sheath capsule 208 during a delivery operation with the valve brim 104 protruding proximally therefrom. The distal sheath capsule 208 is sized and configured such that the valve brim hinge 106 is disposed at the rim or edge of the proximal opening of the distal sheath capsule 208. The prosthetic heart valve 100 is delivered to a deployment site, as discussed, e.g., with respect to FIGS. 2A-2F.

After a failed valve deployment, the inner compression shaft 205 is used to draw the prosthetic heart valve 100 back into the distal sheath capsule 208 as far as possible, as shown in FIG. 19A. The valve brim 104 continues to protrude from the distal sheath capsule 208. To ensure that the valve brim 104 can be drawn back across the septum without damage to the patient anatomy, the brim recapture funnel 204 is used to capture the valve brim 104.

During the recapture, the brim recapture funnel 204 is configured with a size such the brim recapture funnel 204 will contact the interior of the valve brim 104. This may be achieved via manufacturing the brim recapture funnel 204 such that the brim recapture funnel 204 is sized to permit contact between the valve brim 104 and the interior of the brim recapture funnel 204 and/or by partially retracting the brim recapture funnel 204 into the introducer sheath 201 to control the expanded diameter of the brim recapture funnel 204. In further embodiments, the brim recapture funnel 204 may be configured with a size such that the interior of the brim recapture funnel 204 may contact the valve brim 104, thereby providing force to the valve brim 104 with the interior walls of the brim recapture funnel 204. In either configuration, the brim recapture funnel 204 contacts the valve brim 104 and, as the valve brim 104 is drawn closer to the brim recapture funnel 204 through relative movement between the inner compression shaft 205 and the outer steerable catheter, the brim recapture funnel 204 pushes the valve brim 104 back towards the distal sheath capsule 208. Due to the valve brim hinge 106, the valve brim 104 is caused to invert or fold back towards the distal sheath capsule 208 due to pressure from the brim recapture funnel 204. FIG. 19B illustrates the valve brim 104 contacting the brim recapture funnel 204, where the valve brim 104 is partially folded back.

FIG. 19C illustrates the valve brim 104 fully folded back over the distal sheath capsule 208. As the distal sheath capsule 208 is brought closer to the brim recapture funnel 204, continued contact between the brim recapture funnel 204 and the valve brim 104 causes the valve brim 104 to fully fold back over the distal sheath capsule 208, hinging at the valve brim hinge 106, at the rim of the distal sheath capsule 208. The brim recapture funnel 204 is then advanced further so as to pass over and around the valve brim. Finally, the brim recapture funnel 204 is collapsed over the valve brim 104 by drawing the outer steerable catheter 202, the inner steerable catheter 203, and the inner compression shaft 205 are back together into the introducer sheath 201. As the brim recapture funnel 204 is pulled into the introducer sheath 201, the force of the introducer sheathe 201 continues to apply a lateral force directed distally to the brim recapture funnel 204, which further causes the brim recapture funnel 204 to collapse around the valve brim 104.

The folding/inverting valve brim 104 may serve to reduce the length of the captured prosthetic heart valve 100 and distal sheath capsule 208. With the valve brim 104 folded back over the distal sheath capsule 208, the total length of the prosthetic heart valve 100 and distal sheath capsule 208 combination is reduced. The reduced length may facilitate withdrawal from a patient's anatomy. Additionally, inverting valve brim 104 may permit the distal sheath capsule 208 to have a shorter length overall. Due to the inversion, a larger portion of the valve brim 104 may be configured or permitted to protrude from the distal sheath capsule 208. Accordingly, the distal sheath capsule 208 may have a shorter length. Further, the valve brim 104, when folded, may increase the consistency of capture and reduce the diameter of the captured prosthetic heart valve 100 and distal sheath capsule 208. The valve brim 104 may collapse in an irregular manner during a recapture process. Such an irregular collapse may cause bulges or irregularities in the brim recapture funnel 204 after capture. When folded back over the distal sheath capsule 208, the valve brim 104 is guided into a uniformly collapsed configuration, reducing potential irregularities in the collapsed configuration. Finally, because the distal ends of the brim recapture funnel 204 contact the interior of the valve brim 104, the brim recapture funnel 204 may have a smaller expanded diameter than in embodiments where the brim recapture funnel 204 captures the exterior of the valve brim 104.

Figure 20A:
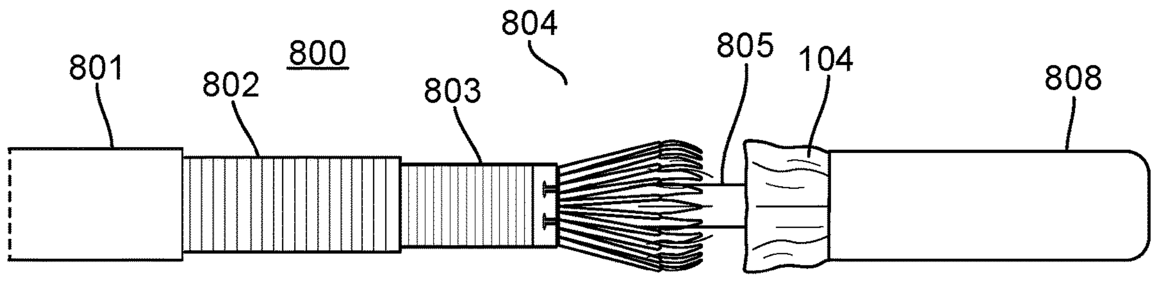
FIG. 20A-20C illustrate stages in a valve recapture operation using a recapture delivery catheter according to embodiments hereof.
Figure 20B:
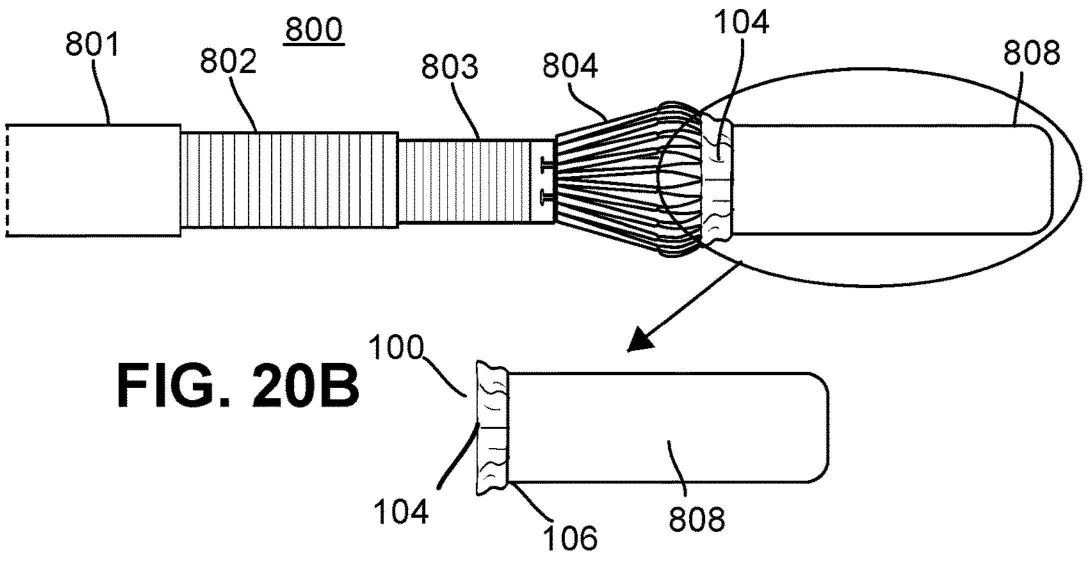
Figure 20C:
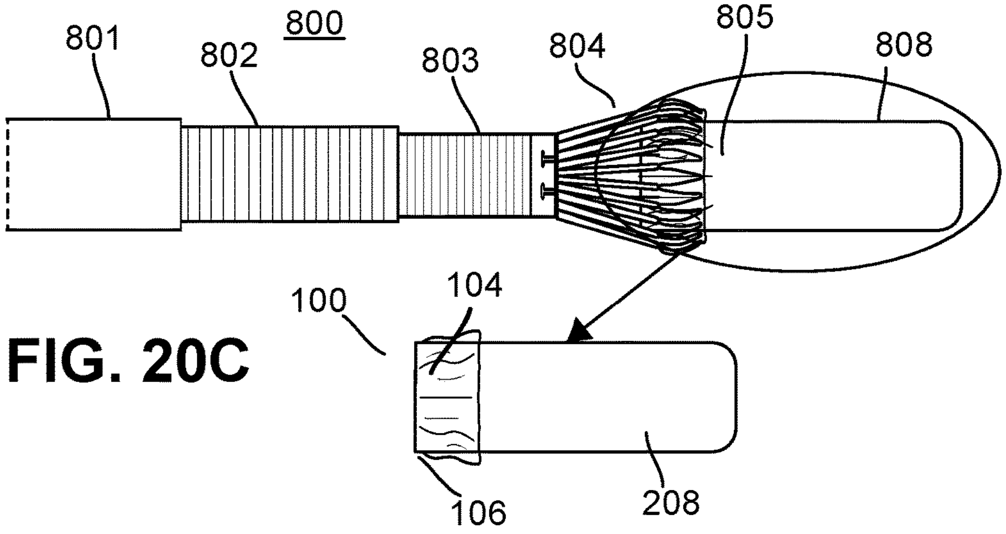

FIGS. 20A-C illustrate the use of recapture delivery catheter 800 having a brim recapture funnel 804 coupled to an inner steerable catheter 803 in a valve brim inversion technique to recapture the prosthetic heart valve 100. As discussed above, the recapture delivery catheter 800 includes an outer steerable catheter 802, an inner steerable catheter 803, a brim recapture funnel 804, an inner compression shaft 805, and a distal sheath capsule 808. The brim recapture funnel 804 is coupled to/located on the inner steerable catheter 803. The prosthetic heart valve 100 is disposed within the distal sheath capsule 808 during a delivery operation with the valve brim 104 protruding. The distal sheath capsule 808 is sized and configured such that the valve brim hinge 106 is disposed at the rim of the distal sheath capsule 808. The prosthetic heart valve 100 is delivered to a deployment site, as discussed, e.g., with respect to FIGS. 2A-2F.

After a failed valve deployment, the inner compression shaft 805 is used to draw the prosthetic heart valve 100 back into the distal sheath capsule 808 as far as possible, as shown in FIG. 20A. The valve brim 104 continues to protrude proximally from the distal sheath capsule 808. To ensure that the valve brim 104 can be drawn back across the septum without damage to the patient anatomy, the brim recapture funnel 804 is used to capture the valve brim 104.

During the recapture, the brim recapture funnel 804 is configured with a size such the brim recapture funnel 804 will contact the interior of the valve brim 104. This may be achieved via manufacturing the brim recapture funnel 804 such that the brim recapture funnel 804 is sized to permit contact between the valve brim 104 and the interior of the brim recapture funnel 804 and/or by partially retracting the brim recapture funnel 804 into the introducer sheath 801 to control the expanded diameter of the brim recapture funnel 804. In further embodiments, the brim recapture funnel 804 may be configured with a size such that the interior of the brim recapture funnel 804 may contact the valve brim 104, thereby providing force to the valve brim 104 with the interior walls of the brim recapture funnel 804. In either configuration, the brim recapture funnel 804 contacts the valve brim 104 and, as the valve brim 104 is drawn closer to the brim recapture funnel 804 through relative movement between the inner compression shaft 805 and the inner steerable catheter 803, the brim recapture funnel 804 pushes the valve brim 104 back towards the distal sheath capsule 808. Due to the valve brim hinge 106, the valve brim 104 is able to fold or hinge back towards the distal sheath capsule 808. FIG. 20B illustrates the valve brim 104 contacting the brim recapture funnel 804, where the valve brim 104 is partially folded back.

FIG. 20C illustrates the valve brim 104 fully folded back over the distal sheath capsule 808. As the distal sheath capsule 808 is brought closer to the brim recapture funnel 804, continued contact between the brim recapture funnel 804 and the valve brim 104 causes the valve brim 104 to fully fold back over the distal sheath capsule 808, hinging at the valve brim hinge 106, at the rim of the distal sheath capsule 808. The brim recapture funnel 804 is then advanced further so as to pass over and around the inverted valve brim 104. The brim recapture funnel 804 is then collapsed over the valve brim 104 by drawing the inner steerable catheter 803 and the inner compression shaft 805 back together into the outer steerable catheter 802 for recovery of the prosthetic heart valve 100. As the brim recapture funnel 804 is pulled into the outer steerable catheter 802, the force provided continues to applies a lateral force directed distally to the brim recapture funnel 804, which further causes the brim recapture funnel 804 to collapse around the valve brim 104.

As used with the recapture delivery catheter 800, the prosthetic heart valve 100 having a folding valve brim 104 provides similar advantages to those discussed above with respect to use with the recapture delivery catheter 200. With the valve brim 104 folded back over the distal sheath capsule 808, the total length of the prosthetic heart valve 100 and distal sheath capsule 808 combination is reduced. Further, the length of the distal sheath capsule 808 itself may be reduced. Additionally, the valve brim 104, when folded, may increase the consistency of capture and reduce the diameter of the captured prosthetic heart valve 100 and distal sheath capsule 208. Finally, the brim recapture funnel 804 may be reduced in diameter.

Figure 21:
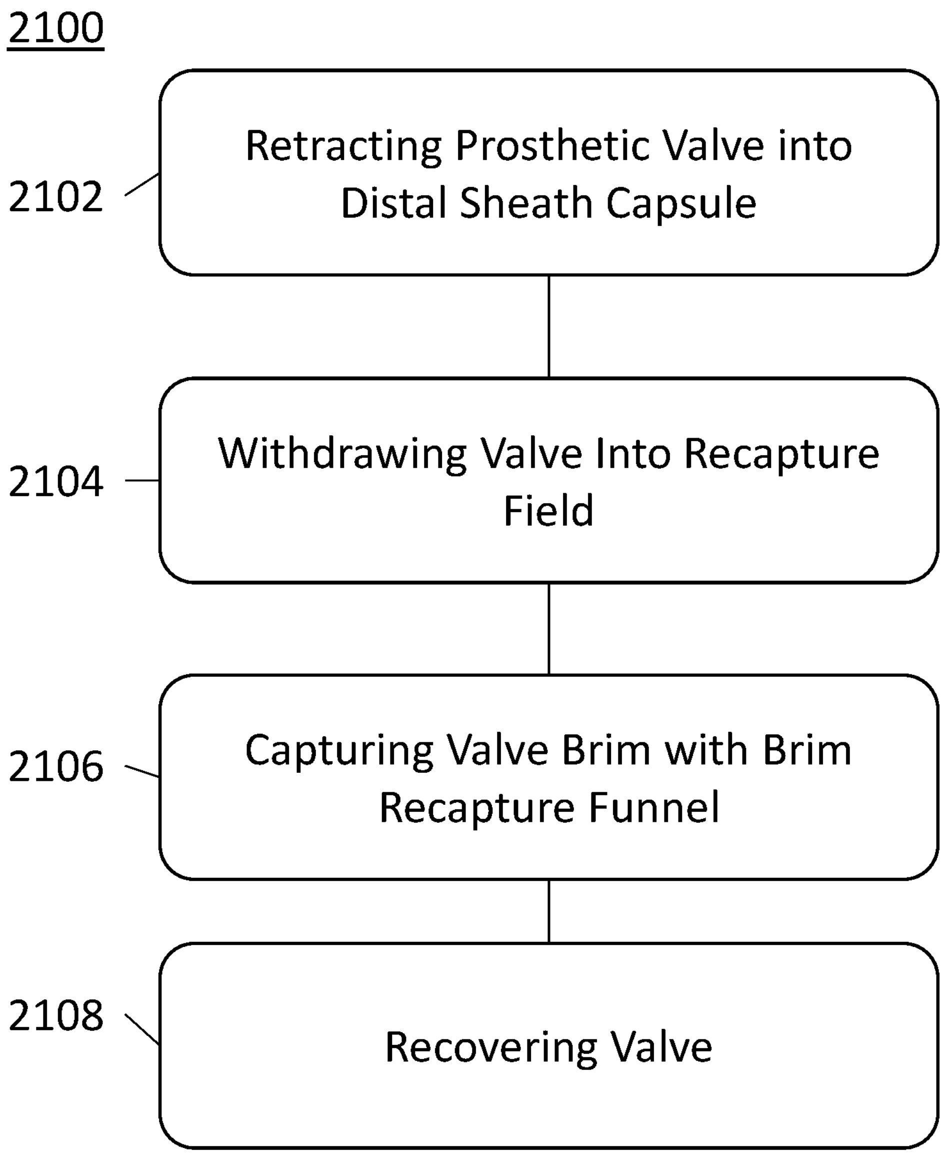
FIG. 21 is a flow chart illustrating operations of a valve recapture process.

FIG. 21 is a flow chart of a prosthetic heart valve recapture process 2100. The devices and structures described herein may be used to recapture a prosthetic heart valve after a failed deployment. Methods of recapturing a prosthetic heart valve described below are consistent with recapture delivery catheters and prosthetic heart valves as discussed herein. In particular, the process 2100 is compatible with both recapture delivery catheters having brim recapture funnels mounted to either an outer steerable catheter (such as the recapture delivery catheter 200) or an inner steerable catheter (such as the recapture delivery catheter 800). It is not necessary that the following operations of process 2100 occur in the order in which they are described. The prosthetic heart valve recapture process 2100 may be used after a failed prosthetic heart valve deployment.

In an operation 2102 of the prosthetic heart valve recapture process 2100, the prosthetic heart valve is retracted into the distal sheath capsule of the recapture delivery catheter. Retracting the prosthetic heart valve into the distal sheath capsule may be performed through activation of a hydraulic system of an inner compression member of the recapture delivery catheter and/or through any other suitable means. After retraction, the valve brim remains protruding from the distal sheath capsule.

In an operation 2104 of the prosthetic heart valve recapture process 2100, the valve brim is withdrawn into a recapture field of the brim recapture funnel. Withdrawing the valve brim into the recapture field of the brim recapture funnel is performed by relative movement between the inner compression member and either the outer steerable catheter or the inner steerable catheter. In embodiments that include a brim recapture funnel located on the outer steerable catheter, relative movement between the inner compression member and the outer steerable catheter is employed to withdraw the valve brim closer to the brim recapture funnel such that is in the recapture field of the brim recapture funnel. In embodiments that include a brim recapture funnel located on the inner steerable catheter, relative movement between the inner compression member and the inner steerable catheter is employed to withdraw the valve brim closer to the brim recapture funnel such that is in the recapture field of the brim recapture funnel.

In an operation 2106 of the prosthetic heart valve recapture process 2100, the valve brim of the prosthetic heart valve is captured by collapsing the brim recapture funnel. In embodiments that include a brim recapture funnel located on the outer steerable catheter, capturing the valve brim with the brim recapture is performed by withdrawing the outer steerable catheter and brim recapture funnel, the inner steerable catheter, the inner compression member, and the distal sheath capsule into the introducer sheath while maintaining the valve brim within the recapture field of the brim recapture funnel. As the outer steerable catheter is pulled into the introducer sheath, longitudinal force on the brim recapture funnel causes it to collapse, thereby capturing the valve brim, as described in greater detail with respect to FIGS. 7A-7F. In embodiments that include a brim recapture funnel located on the inner steerable catheter, capturing the valve brim with the brim recapture is performed by withdrawing the inner steerable catheter and brim recapture funnel, the inner compression member, and the distal sheath capsule into the outer steerable catheter while maintaining the valve brim within the recapture field of the brim recapture funnel. As the inner steerable catheter is pulled into the outer steerable catheter, longitudinal force on the brim recapture funnel causes it to collapse, thereby capturing the valve brim within the brim recapture funnel. As described in greater detail with respect to FIGS. 13A-13D.

In an operation 2108 of the prosthetic heart valve recapture process 2100, recovering the prosthetic heart valve and all elements of the recapture delivery catheter is performed by withdrawing these into the introducer sheath and recovering them from the patient anatomy via the introducer sheath.

Figure 22:
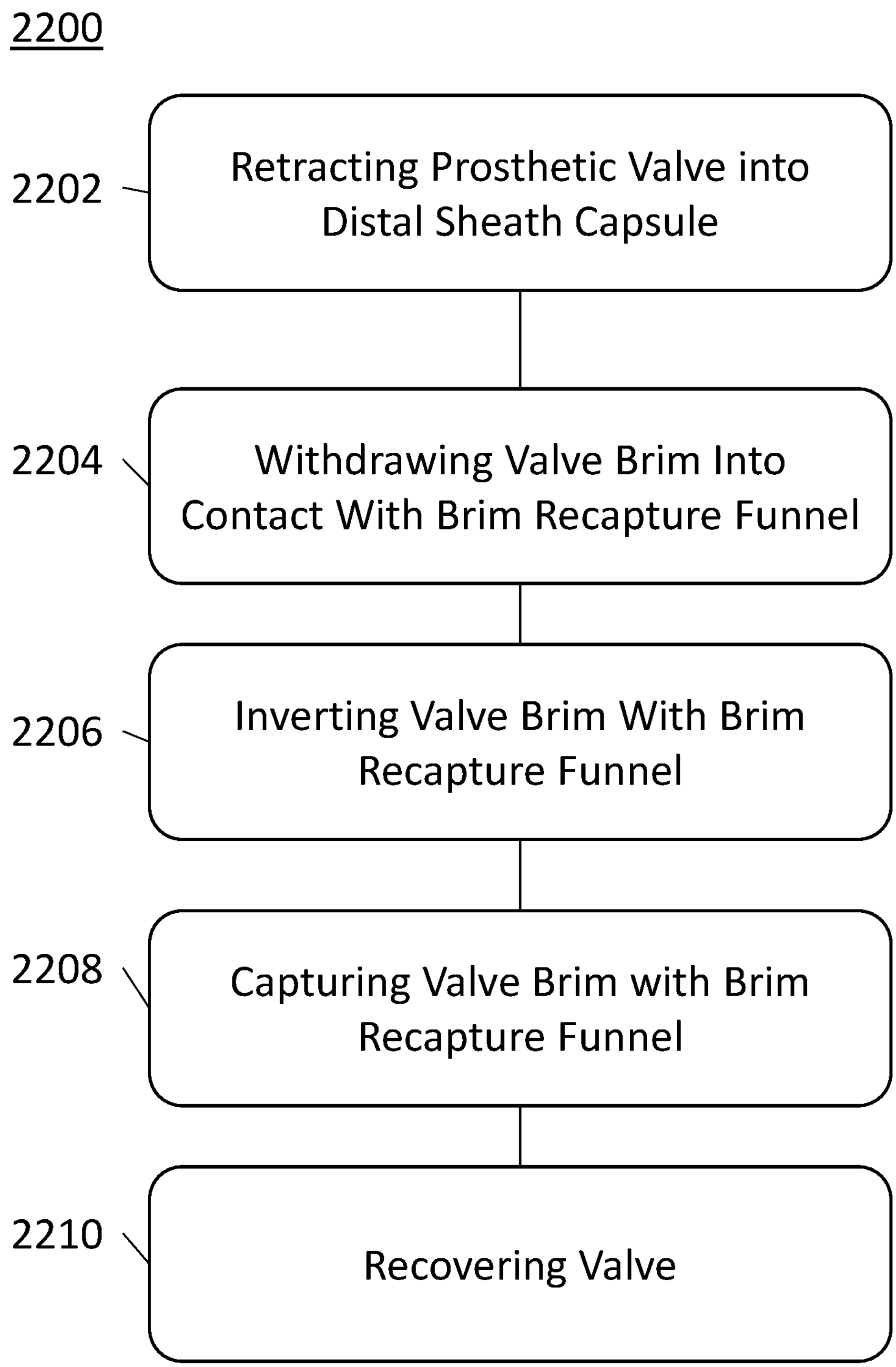
FIG. 22 is a flow chart illustrating operations of a valve recapture process.

FIG. 22 is a flow chart of a prosthetic heart valve recapture process 2200. The devices and structures described herein may be used to recapture a prosthetic heart valve after a failed deployment. Methods of recapturing a prosthetic heart valve described below are consistent with recapture delivery catheters and prosthetic heart valves as discussed herein. In particular, the process 2200 is compatible with both recapture delivery catheters having brim recapture funnels mounted to either an inner steerable catheter (e.g., recapture delivery catheter 800) or an outer steerable catheter (e.g., recapture delivery catheter 200) and the prosthetic heart valve 100 having a foldable valve brim 104. It is not necessary that the following operations of process 2200 occur in the order in which they are described.

In an operation 2202 of the prosthetic heart valve recapture process 2200, the prosthetic heart valve is retracted into the distal sheath capsule of the recapture delivery catheter. Retracting the prosthetic heart valve into the distal sheath capsule may be performed through activation of a hydraulic system of an inner compression member of the recapture delivery catheter and/or through any other suitable means. After retraction, the valve brim remains protruding from the distal sheath capsule.

In an operation 2204 of the prosthetic heart valve recapture process 2200, the brim recapture funnel is brought into contact with the interior of the valve brim. Withdrawing the valve brim into contact with the brim recapture funnel is performed by relative movement between the inner compression member and either the outer steerable catheter or the inner steerable catheter. In embodiments that include a brim recapture funnel located on the outer steerable catheter, relative movement between the inner compression member and the outer steerable catheter is employed to withdraw the valve brim into the brim recapture funnel such that is in contact with the interior of the brim recapture funnel. In embodiments that include a brim recapture funnel located on the inner steerable catheter, relative movement between the inner compression member and the inner steerable catheter is employed to withdraw the valve brim into the brim recapture funnel such that is in contact with the interior of the brim recapture funnel.

In an operation 2206 of the prosthetic heart valve recapture process 2200, inverting the valve brim with the brim recapture funnel is achieved by continuing the relative movement between the brim recapture funnel (located on either the outer steerable catheter or the inner steerable catheter) and the inner compression member (attached to the distal sheath capsule). The brim recapture funnel is advanced against the valve brim, causing it to fold over or invert by hinging at the valve brim hinge between the prosthetic heart valve stent and the valve brim. The brim recapture funnel is then further advanced with respect to the valve brim such that the brim recapture funnel passes over and around the valve brim.

In an operation 2208 of the prosthetic heart valve recapture process 2100, the valve brim of the prosthetic heart valve is captured by collapsing the brim recapture funnel. In embodiments that include a brim recapture funnel located on the outer steerable catheter, capturing the valve brim with the brim recapture is performed by withdrawing the outer steerable catheter and brim recapture funnel, the inner steerable catheter, the inner compression member, and the distal sheath capsule into the introducer sheath while maintaining the valve brim within the recapture field of the brim recapture funnel. As the outer steerable catheter is pulled into the introducer sheath, longitudinal force on the brim recapture funnel causes it to collapse, thereby capturing the valve brim, e.g., as described in greater detail with respect to FIGS. 19A-19C. In embodiments that include a brim recapture funnel located on the inner steerable catheter, capturing the valve brim with the brim recapture is performed by withdrawing the inner steerable catheter and brim recapture funnel, the inner compression member, and the distal sheath capsule into the outer steerable catheter while maintaining the valve brim within the recapture field of the brim recapture funnel. As the inner steerable catheter is pulled into the outer steerable catheter, longitudinal force on the brim recapture funnel causes it to collapse, thereby capturing the valve brim within the brim recapture funnel, e.g., as described in greater detail with respect to FIGS. 20A-20C.

In an operation 2210 of the prosthetic heart valve recapture process 2200, recovering the prosthetic heart valve and all elements of the recapture delivery catheter is performed by withdrawing these into the introducer sheath and recovering them from the patient anatomy via the introducer sheath.

The foregoing description has been presented for purposes of illustration and enablement and is not intended to be exhaustive or to limit the invention to the precise form disclosed. Other modifications and variations are possible in light of the above teachings. The embodiments and examples were chosen and described in order to best explain the principles of the invention and its practical application and to thereby enable others skilled in the art to best utilize the invention in various embodiments and various modifications as are suited to the particular use contemplated. It is intended that the appended claims be construed to include other alternative embodiments of the invention.

What is claimed is:

1. A catheter for deploying a self-expanding prosthetic heart valve, comprising:

an outer steerable catheter;

an inner steerable catheter disposed within the outer steerable catheter;

an inner compression shaft disposed within the inner steerable catheter;

a distal sheath capsule configured to radially contain the self-expanding prosthetic heart valve and connected to the inner compression shaft, wherein the distal sheath capsule is configured to move distally to expose the self-expanding prosthetic heart valve; and a brim recapture funnel configured to recapture a valve brim of the self-expanding prosthetic heart valve.

2. The catheter of claim 1, wherein the brim recapture funnel is disposed on the inner steerable catheter.

3. The catheter of claim 2, wherein the brim recapture funnel is configured for collapse by withdrawing the inner steerable catheter into the outer steerable catheter.

4. The catheter of claim 2, wherein:

the brim recapture funnel includes a plurality of paddles attached at a base of the brim recapture funnel, the inner steerable catheter includes a compression shaft collar having a plurality of mounting slots located therein configured to accommodate the plurality of paddles, the compression shaft collar being disposed within a distal end of the inner steerable catheter to mechanically jail the plurality of paddles and secure the brim recapture funnel.

5. The catheter of claim 4, wherein the brim recapture funnel is configured for collapse by withdrawing the outer steerable catheter into an introducer sheath.

6. The catheter of claim 1, wherein the brim recapture funnel is disposed on the outer steerable catheter.

7. The catheter of claim 6, wherein:

the brim recapture funnel includes a plurality of paddles attached at a base of the brim recapture funnel, the outer steerable catheter includes a plurality of mounting slots located therein configured to accommodate the plurality of paddles and a collar disposed at a distal end of the outer steerable catheter over the plurality of mounting slots to mechanically jail the plurality of paddles and secure the brim recapture funnel.

8. The catheter of claim 1, wherein the brim recapture funnel is configured with an expanded diameter greater than a diameter of the valve brim.

9. The catheter of claim 1, wherein the brim recapture funnel is configured with an expanded diameter greater than a diameter of the distal sheath capsule and smaller than a diameter of the valve brim.

10. The catheter of claim 1, wherein the brim recapture funnel includes:

a proximal contraction section including a first plurality of members connected by a first plurality of distal flexible joints and a first plurality of proximal flexible joints and configured to expand through hinging of the first plurality of distal flexible joints and the first plurality of proximal flexible joints, a distal contraction section including a second plurality of members connected by a second plurality of distal flexible joints and a second plurality of proximal flexible joints and configured to expand through hinging of the second plurality of distal flexible joints and the second plurality of proximal flexible joints, and a midsection including a plurality of bars connecting the first plurality of distal flexible joints to the second plurality of proximal flexible joints.

11. The catheter of claim 1, further comprising:

the self-expanding prosthetic heart valve disposed within the distal sheath capsule, wherein the valve brim of the self-expanding prosthetic heart valve protrudes from a proximal end of the distal sheath capsule in a delivery configuration.

12. The catheter of claim 11, wherein in the delivery configuration, the brim recapture funnel is disposed under the valve brim.

13. A method of recapturing a self-expanding prosthetic heart valve with a delivery catheter, the method comprising:

retracting the self-expanding prosthetic heart valve into a distal sheath capsule of the delivery catheter such that a valve brim of the self-expanding prosthetic heart valve protrudes from the distal sheath capsule;

withdrawing the valve brim into a recapture field of a brim recapture funnel of the delivery catheter;

collapsing the brim recapture funnel over the valve brim to capture the valve brim; and withdrawing the delivery catheter and the self-expanding prosthetic heart valve from patient anatomy;

wherein collapsing the brim recapture funnel is performed by withdrawing the brim recapture funnel, attached to an inner steerable catheter of the delivery catheter, into an outer steerable catheter of the delivery catheter.

14. A method of recapturing a self-expanding prosthetic heart valve with a delivery catheter, the method comprising:

retracting the self-expanding prosthetic heart valve into a distal sheath capsule of the delivery catheter such that a valve brim of the self-expanding prosthetic heart valve protrudes from the distal sheath capsule;

withdrawing the valve brim into a recapture field of a brim recapture funnel of the delivery catheter;

collapsing the brim recapture funnel over the valve brim to capture the valve brim; and withdrawing the delivery catheter and the self-expanding prosthetic heart valve from patient anatomy;

wherein collapsing the brim recapture funnel is performed by withdrawing the brim recapture funnel, attached to an outer steerable catheter of the delivery catheter, into an introducer sheath.

15. A method of recapturing a self-expanding prosthetic heart valve with a delivery catheter, the method comprising:

retracting the self-expanding prosthetic heart valve into a distal sheath capsule of the delivery catheter such that a valve brim of the self-expanding prosthetic heart valve protrudes from the distal sheath capsule;

withdrawing the valve brim into contact with a brim recapture funnel of the delivery catheter;

inverting the valve brim over the distal sheath capsule through force provided by the brim recapture funnel;

capturing the valve brim by advancing the brim recapture funnel relative to the valve brim;

collapsing the brim recapture funnel over the valve brim to capture the valve brim; and withdrawing the delivery catheter and the self-expanding prosthetic heart valve from patient anatomy.

16. The method of claim 15, wherein withdrawing the valve brim into contact with the brim recapture funnel includes contacting an interior of the valve brim with the brim recapture funnel.

17. The method of claim 15, wherein withdrawing the valve brim into contact with the brim recapture funnel includes contacting an interior of the brim recapture funnel with the valve brim.

* * * * *